US011467236B2

(12) United States Patent
Ohishi et al.

(10) Patent No.: US 11,467,236 B2
(45) Date of Patent: Oct. 11, 2022

(54) BIOLOGICAL INFORMATION MONITORING APPARATUS AND MRI APPARATUS

(71) Applicant: CANON MEDICAL SYSTEMS CORPORATION, Otawara (JP)

(72) Inventors: Takafumi Ohishi, Yokohama (JP); Sadanori Tomiha, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 307 days.

(21) Appl. No.: 16/813,865

(22) Filed: Mar. 10, 2020

(65) Prior Publication Data

US 2020/0294658 A1  Sep. 17, 2020

(30) Foreign Application Priority Data

Mar. 12, 2019 (JP) .............................. JP2019-044664
Jan. 8, 2020 (JP) .............................. JP2020-001583

(51) Int. Cl.
*G01R 33/34* (2006.01)
*A61B 5/055* (2006.01)
(Continued)

(52) U.S. Cl.
CPC ........ *G01R 33/34038* (2013.01); *A61B 5/055* (2013.01); *G01R 33/34046* (2013.01);
(Continued)

(58) Field of Classification Search
CPC .............. A61B 5/055; G01R 33/34038; G01R 33/34046; G01R 33/5612; G16H 40/63; G16H 30/20
See application file for complete search history.

(56) References Cited

U.S. PATENT DOCUMENTS 7,037,267 B1 * 5/2006 Lipson ................. A61B 8/4416
600/468
8,489,174 B2 7/2013 Stemmer
(Continued)

FOREIGN PATENT DOCUMENTS

JP 2009-055997 A 3/2009
WO WO 2018/232414 A1 12/2018

OTHER PUBLICATIONS

Extended European Search Report dated Jul. 28, 2020 in Patent Application No. 20162178.6, 9 pages.
(Continued)

*Primary Examiner* — Dixomara Vargas
(74) *Attorney, Agent, or Firm* — Oblon, McClelland, Maier & Neustadt, L.L.P.

(57) ABSTRACT

In one embodiment, a biological information monitoring apparatus includes: an antenna assembly including at least one antenna, the antenna assembly being configured to be disposed close to an abject; a signal generator configured to generate a high-frequency signal; a coupling-amount detection circuit configured to detect coupling amount of near-field coupling due to an electric field between the object and the at least one antenna by using the high-frequency signal; and a displacement detection circuit configured to detect a physical displacement of the object based on change in the coupling amount of near-field coupling.

20 Claims, 21 Drawing Sheets

(51) Int. Cl.
*G01R 33/561* (2006.01)
*G16H 30/20* (2018.01)
*G16H 40/63* (2018.01)

(52) U.S. Cl.
CPC ......... *G01R 33/5612* (2013.01); *G16H 30/20* (2018.01); *G16H 40/63* (2018.01)

(56) References Cited

U.S. PATENT DOCUMENTS

| | | | | |
|---|---|---|---|---|
| 2011/0012431 | A1* | 1/2011 | Karalis | H02J 50/12 |
| | | | | 307/104 |
| 2011/0121834 | A1* | 5/2011 | Soutome | G01R 33/365 |
| | | | | 324/318 |
| 2014/0306706 | A1* | 10/2014 | Lazar | G01R 33/288 |
| | | | | 324/309 |
| 2016/0254704 | A1* | 9/2016 | Hansen | H02J 50/12 |
| | | | | 307/104 |
| 2017/0033605 | A1* | 2/2017 | Nakamura | H02J 7/025 |
| 2017/0063143 | A1* | 3/2017 | Hoarau | A41F 9/002 |
| 2017/0135600 | A1 | 5/2017 | Chien et al. | |
| 2017/0163101 | A1* | 6/2017 | Muratov | H02J 50/80 |
| 2018/0109149 | A1* | 4/2018 | Murayama | H01F 38/14 |
| 2019/0041476 | A1* | 2/2019 | Otake | G01R 33/343 |
| 2019/0331745 | A1* | 10/2019 | Chen | G01R 33/3628 |
| 2020/0170514 | A1 | 6/2020 | Hui et al. | |
| 2020/0292650 | A1* | 9/2020 | Ohishi | H04B 13/005 |
| 2020/0341083 | A1* | 10/2020 | Ohishi | G01R 33/3692 |
| 2021/0298629 | A1* | 9/2021 | Ohishi | G01R 33/5612 |

OTHER PUBLICATIONS

Yong-Jun An, et al., "Sensitivity Enhanced Vital Sign Detection Based on Antenna Reflection Coefficient Variation" IEEE Transactions on Biomedical Circuits and Systems, vol. 10, No. 2, XP011608579, Apr. 1, 2016, pp. 319-327.

* cited by examiner

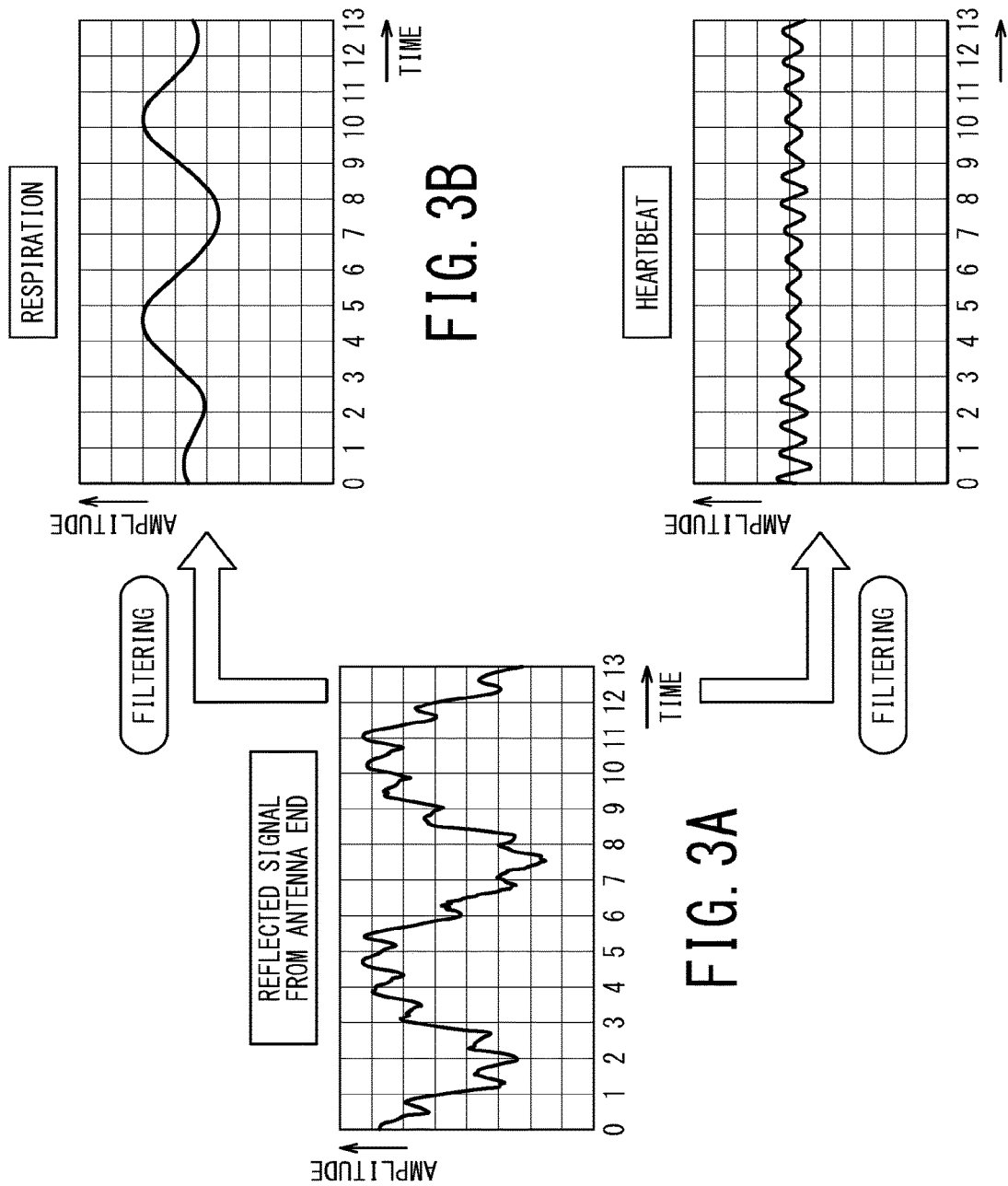

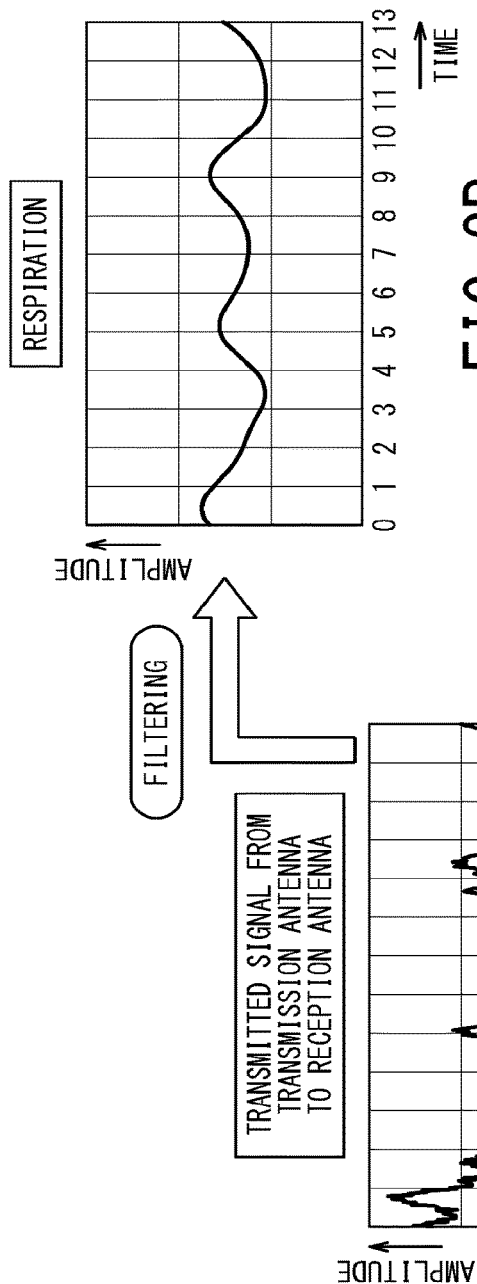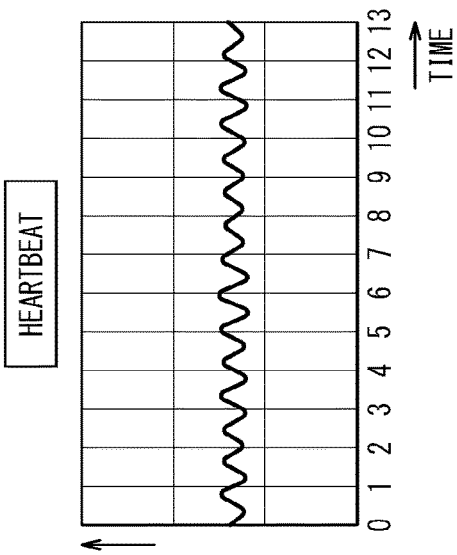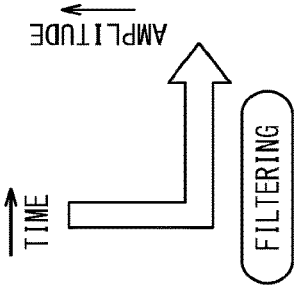

BIOLOGICAL INFORMATION MONITORING APPARATUS AND MRI APPARATUS

CROSS-REFERENCE TO RELATED APPLICATION

This application is based upon and claims the benefit of priority from Japanese Patent Applications No. 2019-044664, filed on Mar. 12, 2019, and No. 2020-001583, filed on Jan. 8, 2020, the entire contents of each of which are incorporated herein by reference.

TECHNICAL FIELD Disclosed Embodiments relate to a biological information monitoring apparatus and magnetic resonance imaging (MRI) apparatus.

BACKGROUND

In imaging using an MRI apparatus, MR (Magnetic Resonance) signals acquired from an object may fluctuate due to body motion such as heartbeat and respiration of a human body. Conventionally, in order to correct influence of heartbeat on the MR imaging, electrodes of an electrocardiograph, for example, are attached to the human body such that imaging timing is adjusted by using signals outputted from the electrocardiograph and/or the acquired data are corrected on the basis of the signals from the electrocardiograph.

However, attaching the electrodes to the human body is a burden on the patient and also causes reduction in work efficiency for a medical imaging technologist.

In another known imaging method, data for monitoring a body motion caused by respiration or breathing are additionally acquired as navigation data aside from data acquisition for generating diagnostic images so that the navigation data are used for correcting the influence of a body motion caused by respiration. However, in this method, extra time is required for acquiring the navigation data, and thus its imaging time becomes longer. From such a viewpoint, there is a demand for a non-contact type body-motion monitoring apparatus that does not impose a burden on the patient.

The non-contact type body-motion monitoring apparatus has been widely demanded not only in imaging using an MRI apparatus but also in the field of health care. There is also a demand for a body-motion monitoring apparatus that can monitor, for example, a cardiac rate and a respiration rate during sleep and/or during driving of a vehicle in a contactless manner without imposing a burden on the human body.

In a conventionally proposed apparatus, a motion of the object is detected by using a radio wave for detecting a heart rate and/or a respiration rate. In this apparatus, a radio wave is transmitted from an antenna to the object, and then, by detecting change in a reflected radio wave from the object, a motion of the object is detected.

However, in the conventional detection apparatus using a radio wave, not only reflected waves from the object but also reflected waves from various structures around the object are simultaneously received, which causes a fading phenomenon and makes it difficult to reliably and stably detect the heartbeat and respiration of the object.

BRIEF DESCRIPTION OF THE DRAWINGS

In the accompanying drawings:

FIG. 3A is a graph for illustrating actually measured values of a reflected signal from an antenna;

FIG. 3B is a graph for illustrating a waveform of respiration extracted from the reflected signal;

FIG. 3C is a graph for illustrating a waveform of heartbeat extracted from the reflected signal;

FIG. 8A is a graph for illustrating actually measured values of a transmitted signal from the transmission antenna to the reception antenna;

FIG. 8B is a graph for illustrating a waveform of respiration extracted from the transmitted signal;

FIG. 8C is a graph for illustrating a waveform of heartbeat extracted from the transmitted signal;

DETAILED DESCRIPTION

First Embodiment

Hereinbelow, the first embodiment of the present invention will be described by referring to the accompanying drawings.

In one embodiment, a biological information monitoring apparatus includes: an antenna assembly including at least one antenna, the antenna assembly being configured to be disposed close to an abject; a signal generator configured to generate a high-frequency signal; a coupling-amount detection circuit configured to detect coupling amount of near-field coupling due to an electric field between the object and the at least one antenna by using the high-frequency signal; and a displacement detection circuit configured to detect a physical displacement of the object based on change in the coupling amount of near-field coupling.

Figure 1:
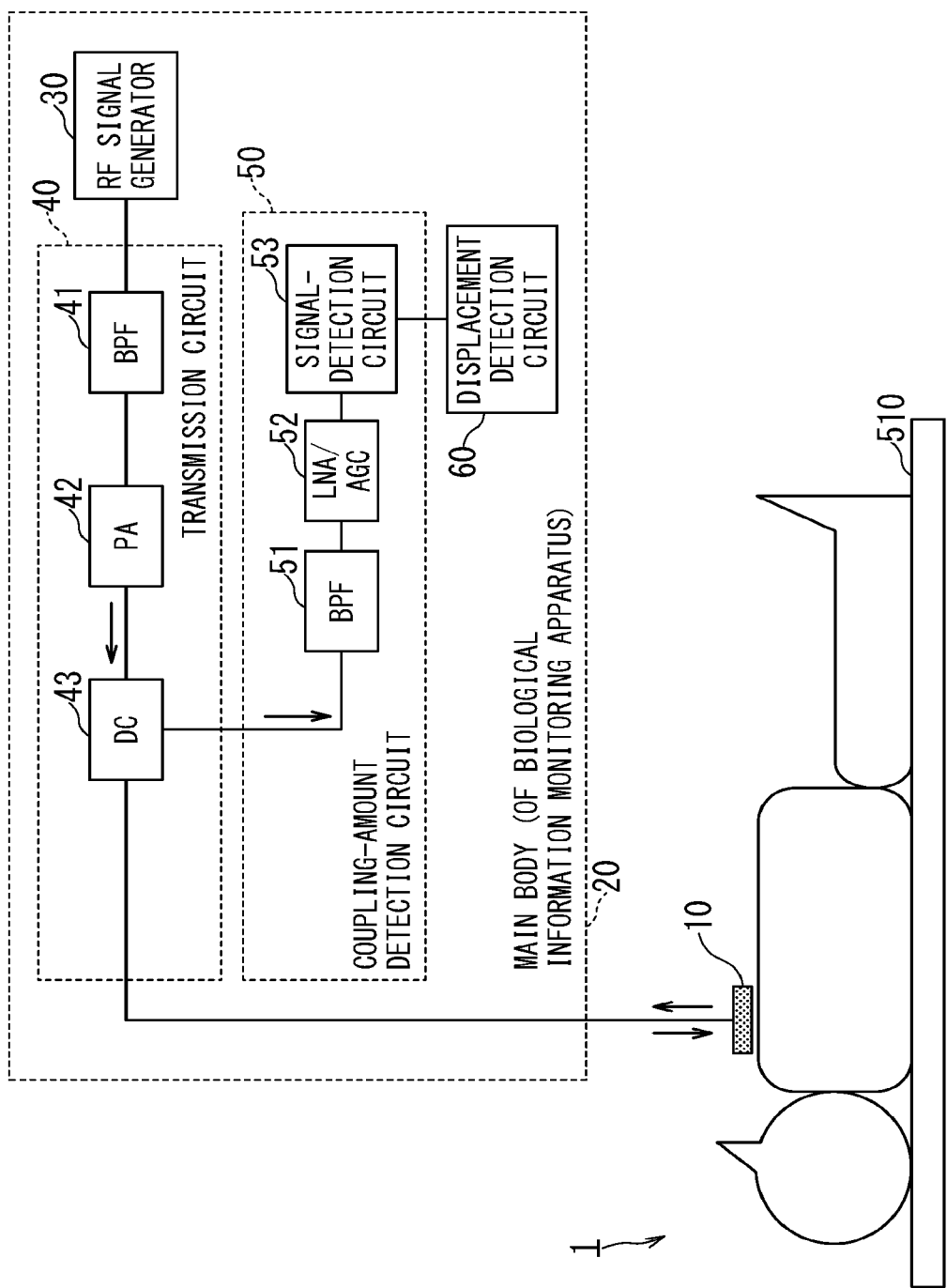
FIG. 1 is a configuration diagram illustrating an overall configuration of a biological information monitoring apparatus according to the first embodiment.

FIG. 1 is a configuration diagram illustrating an overall configuration of a biological information monitoring apparatus 1 according to the first embodiment. The biological information monitoring apparatus 1 includes an antenna 10 and biological-information monitoring main-body 20 (hereinafter, shortly referred to as the main body 20). The antenna 10 is a configuration of an antenna assembly. Since the biological information monitoring apparatus 1 basically includes one antenna in the first embodiment, the antenna assembly is configured as one antenna. In other embodiments described below, the biological information monitoring apparatus 1 may have a plurality of antennas. In such a case, the antenna assembly includes a plurality of antennas.

The antenna 10 is disposed close to an object, which may be usually a human body or a patient. The antenna 10 does not need to be directly adhered to the skin of the object like electrodes of an electrocardiograph, and may be placed on the clothes of the object, for example. Although FIG. 1 illustrates a case where the antenna 10 is disposed on the chest of the object lying on a table 510 of a bed, the posture of the object on which the antenna 10 is disposed, and/or the anatomical part of the object on which the antenna 10 is disposed are not limited to the situation as shown in FIG. 1. For example, the antenna 10 may be disposed on the chest or back of the object in a standing position or may be disposed on the chest or back of the object in a sitting position, for example, during driving of a vehicle.

The main body 20 includes an RF signal generator 30, a transmission circuit 40, a coupling-amount detection circuit 50, and a displacement detection circuit 60.

The RF signal generator (or signal generator, simply) 30 generates a high-frequency signal as a continuous wave. Although the frequency of the high-frequency signal is not limited to a specific frequency, a frequency in the VHF band or in the UHF band may be selected in accordance with the dimensions of the antenna, for example.

The transmission circuit 40 causes the high-frequency signal to pass through a band-pass filter (BPF) 41, then the amplifies the high-frequency signal to a predetermined power by a power amplifier (PA) 42, and then outputs it to the antenna 10 via a directional coupler (DC) 43.

The coupling-amount detection circuit 50 has the function of detecting the amount of near-field coupling caused by the electric field between the object and the antenna 10. For implementing this function, the coupling-amount detection circuit 50 includes a band-pass filter (BPF) 51, a low-noise amplifier (LNA/AGC) 52 with an automatic gain adjustment function, and a signal-detection circuit 53, for example.

The RF signal generator 30, the transmission circuit 40, and the coupling-amount detection circuit 50 can be mounted on, for example, a printed substrate housed in one casing.

Although the high-frequency signal outputted from the directional coupler 43 of the transmission circuit 40 is inputted to the antenna 10, part of this high-frequency signal does not go into the object but is bounced off (reflected) at the input end of the antenna 10 to be returned to the directional coupler 43, and then is branched and inputted to the coupling-amount detection circuit 50.

The coupling-amount detection circuit 50 detects the signal outputted from the branch end of the directional coupler 43 by using the signal-detection circuit 53 so as to measure magnitude of the reflected signal from the antenna 10. Then, detects the amount of near-field coupling is detected on the basis of the measured magnitude of the reflected signal, by the coupling-amount detection circuit 50.

Considering that the power outputted from the transmission circuit 40 to the antenna 10 is a constant value, the coupling-amount detection circuit 50 equivalently detects the S11 parameter indicating the reflection loss (i.e., return loss) of the antenna 10.

Figure 2B:
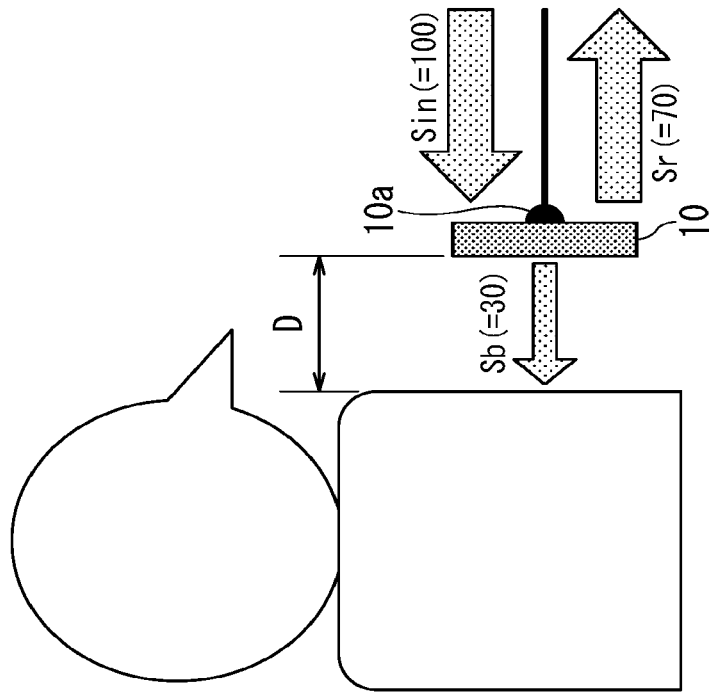
FIG. 2A and FIG. 2B are schematic diagrams illustrating the operation concept of the biological information monitoring apparatus according to the first embodiment.
Figure 2A:
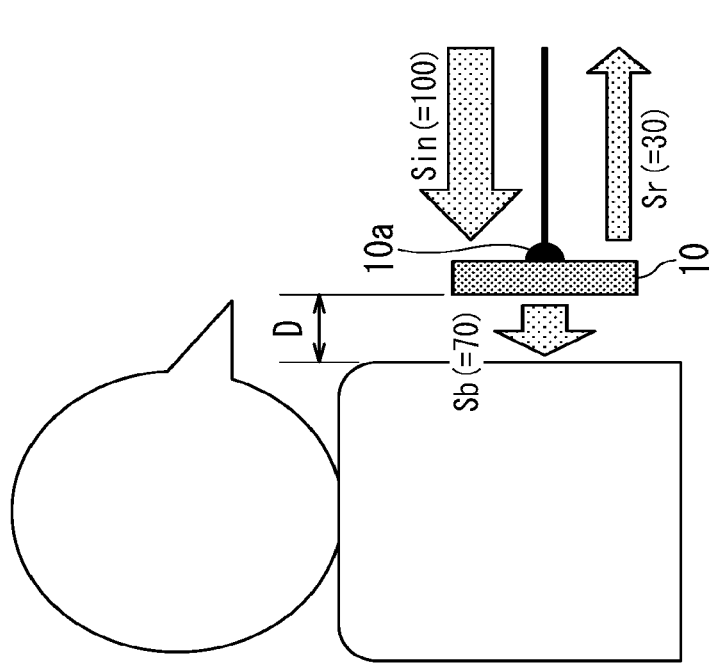

FIG. 2A and FIG. 2B are schematic diagrams illustrating the operation concept of the biological information monitoring apparatus 1 according to the first embodiment. FIG. 2A schematically illustrates the operation when the distance D between the object and the antenna 10 is short, while FIG. 2B schematically illustrates the operation when the distance D between the object and the antenna 10 is long. Note that the object (human body) has electrical conductivity, and thus readily absorbs energy from the antenna 10 when the antenna 10 approaches the object.

Hence, as shown in FIG. 2A, when the distance D between the object and the antenna 10 is short, the energy absorbed by the object increases. This means that the amount of near-field coupling between the object and antenna 10 is large. The power Sin inputted to the antenna 10 is mainly divided into power Sb absorbed by the object and power Sr reflected from the antenna end 10a of the antenna 10. When the distance D is short, the power Sb absorbed by the object increases, while the power Sr reflected from the antenna end 10a decreases accordingly. For example, when the power Sin inputted to the antenna 10 is assumed to be 100, the power Sb absorbed by the object may become 70, and the power Sr reflected from the antenna end 10a may become 30.

This means that the reflected signal from the antenna end 10a decreases and the reflection loss (i.e., return loss) of the antenna 10 also decreases when the distance D between the object and the antenna 10 is short. In other words, the S11 parameter, which is an index of the degree of mismatch of antenna 10, indicates a small value. The S11 parameter is an index represented by the square root of the ratio of the reflected power to the input power that is inputted to the antenna 10.

On the other hand, as shown in FIG. 2B, when the distance D between the object and the antenna 10 is long, the energy to be absorbed by the object decreases. This means that the amount of near-field coupling between the object and antenna 10 is small. As a result, when the distance D is long, the power Sb absorbed by the object decreases, and thus, the power Sr reflected from the antenna end 10a increases, accordingly. For example, when the power Sin inputted to the antenna 10 is assumed to be 100, the power Sb absorbed by the object may become 30, and the power Sr reflected from the antenna end 10a may become 70.

This means that the reflected signal from the antenna end 10a increases and the reflection loss (i.e., return loss) of the antenna 10 also increases when the distance D between the object and the antenna 10 is long. In other words, the S11 parameter, which is an index of the degree of mismatch of antenna 10, indicates a large value.

As described above, when the input power to the antenna 10 is assumed to be constant, the reflected signal from the antenna end 10a changes depending on the distance D between the object and the antenna 10. In other words, the degree of mismatch of the antenna 10 or the value of the S11 parameter also changes depending on the distance D between the object and the antenna 10. Since the distance D between the object and the antenna 10 changes depending on the body motion such as heartbeat and/or respiration, magnitude of the reflected signal from the antenna end 10a or the value of the S11 parameter changes depending on change in body motion such as heartbeat and/or respiration.

The biological information monitoring apparatus 1 of the first embodiment is configured to use above-described characteristics, and detects the magnitude of the reflected signal from the antenna 10 disposed near the object or the value of the S11 parameter so as to detect the body motion such as heartbeat and/or respiration.

FIG. 3A is a graph for illustrating actually measured values of the reflected signal from the antenna 10. In this graph, the horizontal axis indicates time and the vertical axis indicates amplitude of the reflected signal. As shown in FIG. 3A, the reflected signal from the antenna 10 has a waveform in which a short-period fluctuation waveform corresponding to heartbeat is superimposed on a relatively long-period fluctuation waveform corresponding to respiration. The reflected signal from the antenna 10 is detected by the signal-detection circuit 53 of the coupling-amount detection circuit 50, and then is outputted to the displacement detection circuit 60.

The displacement detection circuit 60 may be configured as, for example, a dedicated printed circuit board provided with a processor or may be configured as an information processing apparatus such as a personal computer and a tablet terminal device provided with a display.

The displacement detection circuit 60 performs filtering processing for extracting a frequency component corresponding to a respiratory motion and another frequency component corresponding to heartbeat on the reflected signal detected by the signal-detection circuit 53 so as to generate a respiratory waveform shown in FIG. 3B and a heartbeat waveform shown in FIG. 3C. Additionally or alternatively, the displacement detection circuit 60 may perform Fourier transform on the reflected signal from the antenna 10, then extract the respective frequency components corresponding to the respiratory motion and heartbeat on a frequency space, and then perform inverse Fourier transform on both extracted frequency components so as to generate the respiratory waveform shown in FIG. 3B and the heartbeat waveform shown in FIG. 3C.

The displacement detection circuit 60 may cause an appropriate display to display the generated respiratory waveform and heartbeat waveform, or may analyze the generated respiratory waveform and heartbeat waveform. For example, the displacement detection circuit 60 may analyze the respiratory waveform and/or the heartbeat waveform so as to acquire respiratory and/or cardiac parameters such as a respiratory rate, a respiratory cycle, a cardiac rate, and/or a cardiac cycle. Further, the displacement detection circuit 60 may detect presence/absence of an abnormality in respiration or heartbeat from the acquired respiratory and/or cardiac parameters.

FIG. 4A to FIG. 4D are schematic diagrams for illustrating comparison between a loop antenna and a dipole antenna as the antenna 10 used in the biological information monitoring apparatus 1.

Figure 4C:
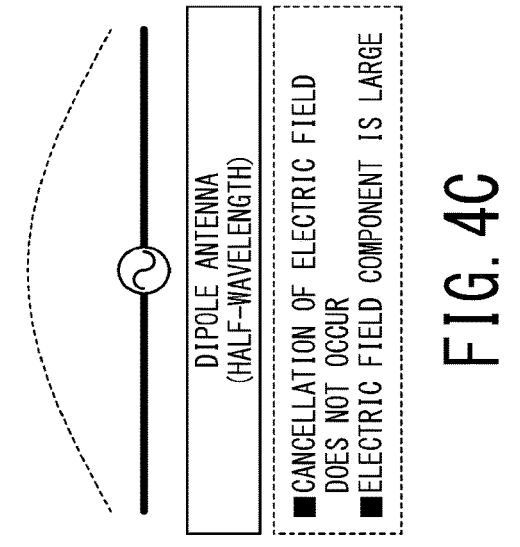
FIG. 4A to FIG. 4D are schematic diagrams for illustrating comparison between a loop antenna and a dipole antenna as the antenna to be used in the biological information monitoring apparatus.
Figure 4D:
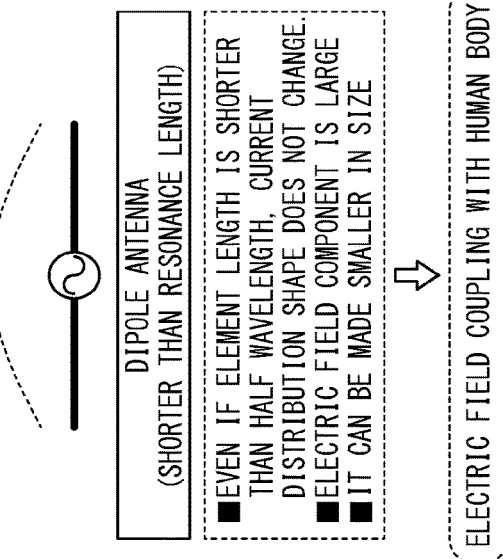
Figure 4A:
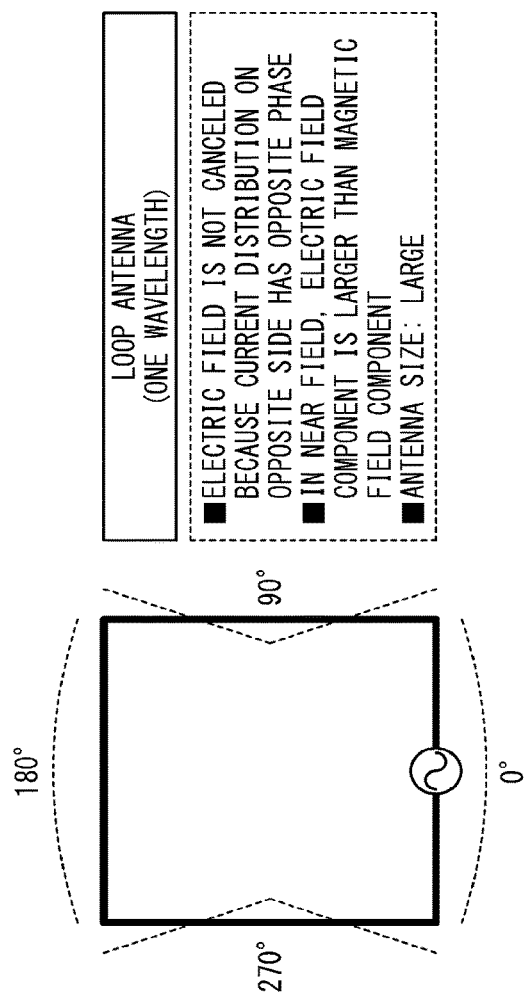

FIG. 4A shows a loop antenna having a loop length of a resonance length, i.e., a one-wavelength loop antenna. In the one-wavelength loop antenna, the electric field is not canceled because the current distribution on the opposite side has an opposite phase. Thus, in the near field, the electric field component becomes larger than the magnetic field component. Although it depends on the frequency to be used, the one-wavelength loop antenna is relatively large in antenna size.

Figure 4B:
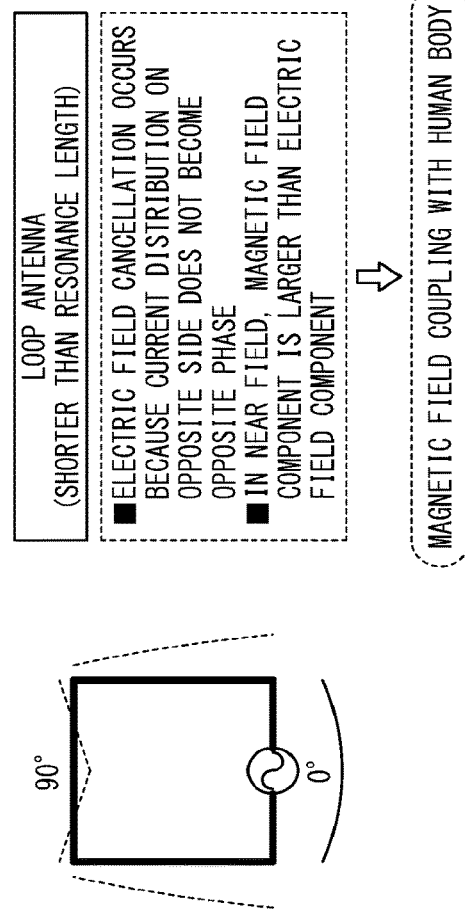

FIG. 4B shows a loop antenna, loop length of which is shorter than the resonance length. In this type of loop antenna, cancellation of the electric field occurs because the current distribution on the opposite side does not become the opposite phase. Thus, in the near field, the magnetic field component becomes larger than the electric field component. Hence, coupling with the human body in the near field is magnetic field coupling. Magnetic field coupling tends to readily pass through the interior of the human body.

FIG. 4C shows a half-wave dipole antenna. In the half-wavelength dipole antenna, there is no cancellation of the electric field, and thus, the electric field component is large in the near field.

FIG. 4D shows a dipole antenna, element length of which is shorter than the resonance length. Even when the element length is shorter than the resonance length (i.e., half wavelength), the current distribution shape does not change. Thus, in the case of this dipole antenna shown in FIG. 4D, the electric field component is large in the near field similarly to the half-wave dipole antenna. The dipole antenna shown in FIG. 4D can be made smaller in size than a half-wave dipole antenna. In the case of this dipole antenna, the electric field component is large in the near field, and thus coupling with the human body in the near field is electric field coupling. Electric field coupling tends to readily propagate on the surface of the body.

From the viewpoint of miniaturization, it is preferred to use a loop antenna having a loop length shorter than the resonance length (FIG. 4B) and/or a dipole antenna shorter than a half wavelength (FIG. 4D), and any one of these two antennas can be used for the biological information monitoring apparatus 1. However, it is recognized that the dipole antenna tends to extract a more detailed electrocardiographic waveform than the loop antenna.

In an usual antenna used for communication, it is required that the reflected signal from the antenna is reduced as much as possible so that the power going out into space is increased as much as possible. Thus, it is considered that the voltage standing wave ratio (VSWR) of the antenna is preferably as close to 1.0 as possible. By contrast, in the biological information monitoring apparatus 1 of the first embodiment, heartbeat and a respiratory motion are detected by detecting the reflected signal from the antenna 10. For this reason, it is rather preferred that there is a reflected signal from the antenna 10 to some extent. Hence, the voltage standing wave ratio (VSWR) of the antenna 10 used in the biological information monitoring apparatus 1 of the first embodiment is preferably set to, for example, a value between 2.0 and 5.0.

FIG. 5A to FIG. 5D are schematic diagrams for illustrating disposition of the antenna 10 used in the first embodiment. Although the number of the antenna 10 of the first embodiment is basically one, many variations are conceivable for disposition and orientation of the antenna 10. As a basic idea, it is preferred to dispose the antenna 10 at a position where the body motion appears as much as possible. In the case of detecting heartbeat, it is preferred to dispose the antenna 10 at a position as close to the heart as possible.

Figure 5A:
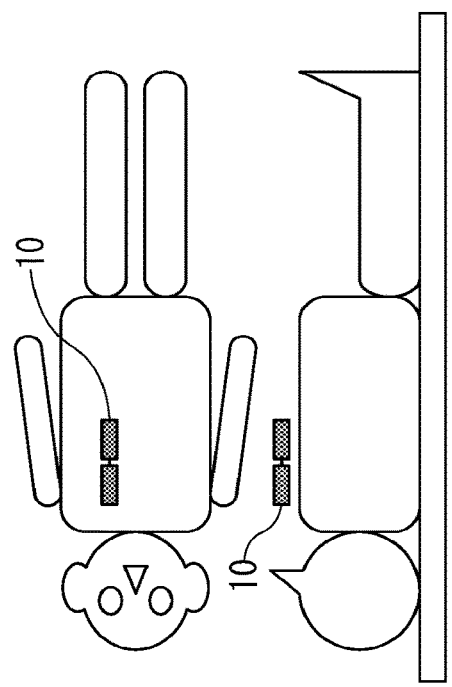
FIG. 5A to FIG. 5D are schematic diagrams for illustrating disposition of the antenna to be used in the first embodiment.
Figure 5B:
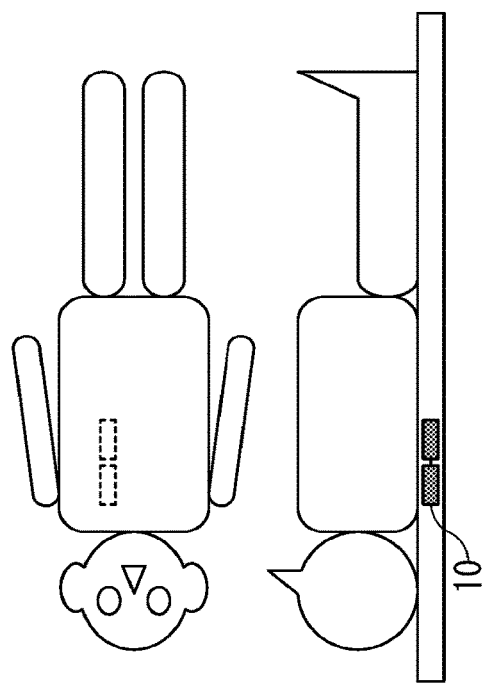

Each of FIG. 5A to FIG. 5D illustrates a dipole antenna as the antenna 10. It is said that the heart moves more in the head-foot direction than in the right-left direction of the object. For this reason, in FIG. 5A, the antenna 10 is disposed near the heart on the anterior side in the anterior-posterior direction of the object, such that the longitudinal direction of the dipole antenna matches the head-foot direction of the object. In FIG. 5B, the antenna 10 is disposed near the heart on the back side (i.e., posterior side) of the object, such that the longitudinal direction of the dipole antenna matches the head-foot direction of the object as well.

Figure 5C:
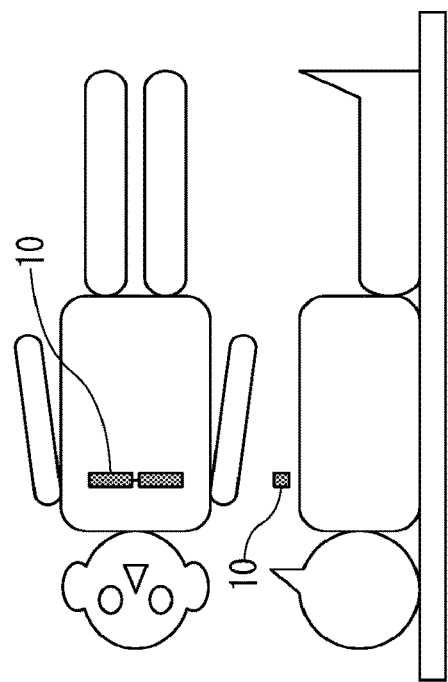
Figure 5D:
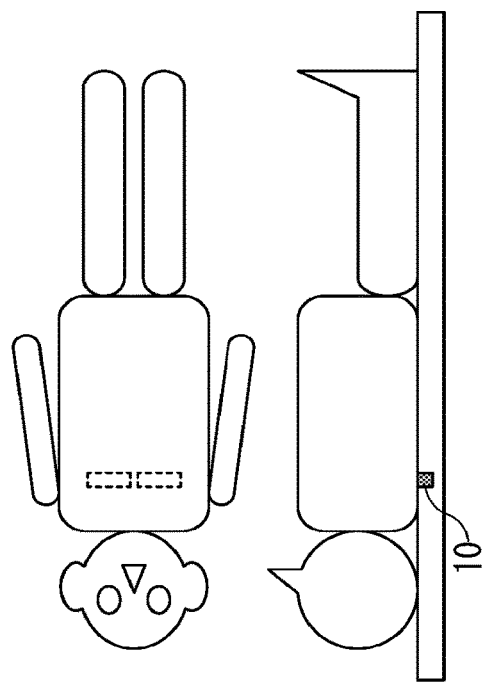

The position of the antenna 10 may be subject to some physical restrictions. For example, when the cardiac rate of the object is measured by using the biological information monitoring apparatus 1 during imaging of the object with the use of an MRI apparatus 100, an RF coil (i.e., local coil or surface coil) 200 of the MRI apparatus 100 is disposed on the object. When the RF coil 200 is a chest coil, for example, the antenna 10 is disposed at a position avoiding the chest coil and as close to the heart as possible, as shown in FIG. 5C. When the antenna 10 is disposed on the back side and the RF coil 200 is a spine coil, for example, the antenna 10 is disposed at a position avoiding the spine coil and as close to the heart as possible, as shown in FIG. 5D.

As described above, in the biological information monitoring apparatus 1 according to the first embodiment, a body motion such as heartbeat and/or respiration is detected as change in coupling amount of the near-field coupling between the antenna 10 and the human body. This change in coupling amount of the near-field coupling is measured as change in the reflected signal reflected from the input end of the antenna 10 or as change in the value of the S11 parameter, which is the reflection loss of the antenna 10. The "input end" of the antenna 10 may be referred to as an "input terminal" of the antenna 10. Thus, while the detection method of the biological information monitoring apparatus 1 according to the first embodiment is a non-contact detection method with the use of radio waves, the biological information monitoring apparatus 1 is less susceptible to fading due to interference with reflected waves from structures around the object, for example, a gantry structure of an MRI apparatus or various devices in an examination room. Thus, the biological information monitoring apparatus 1 can detect heartbeat and/or a respiratory motion with high reliability.

Second Embodiment

Figure 6:
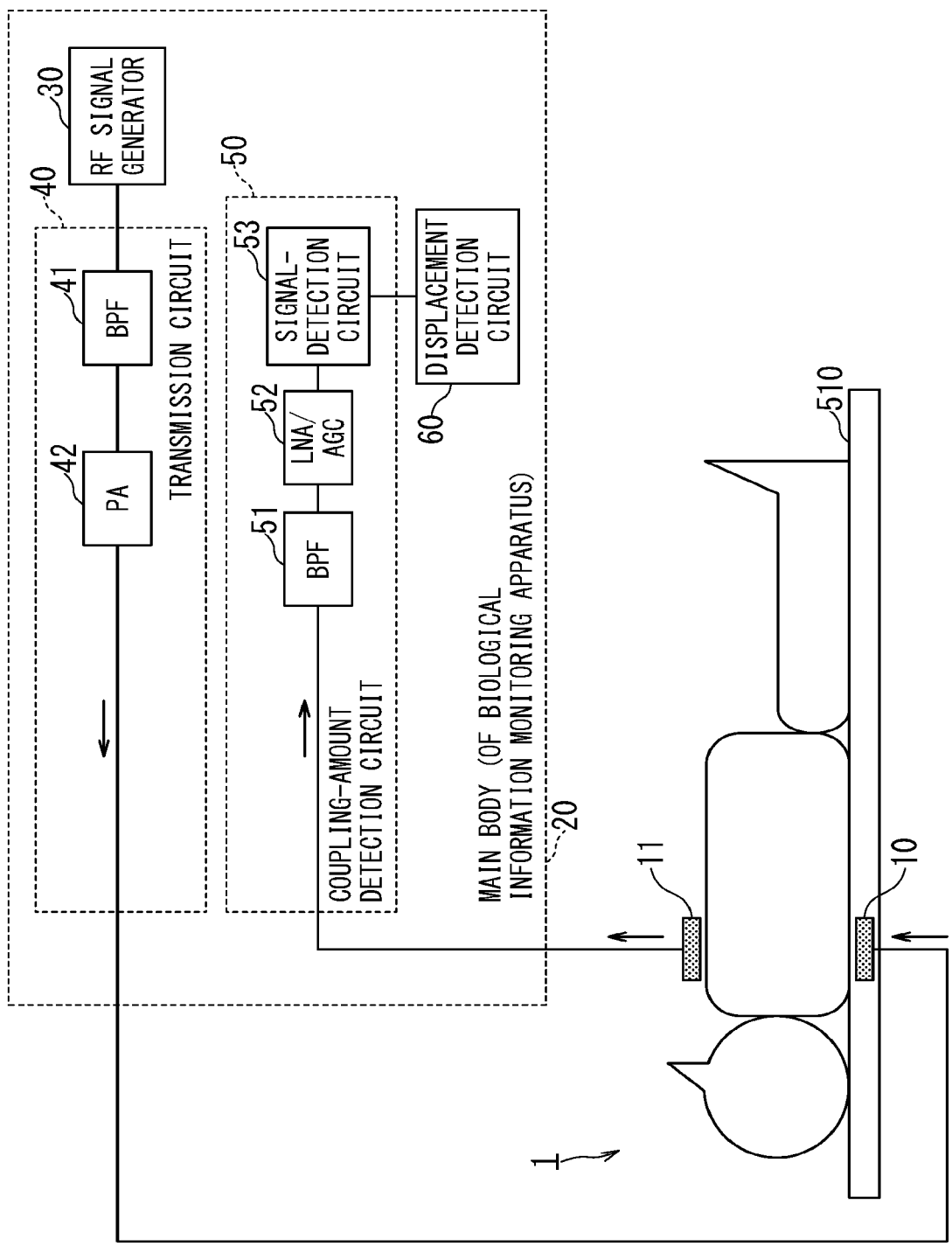
FIG. 6 is a block diagram illustrating an overall configuration of the biological information monitoring apparatus according to the second embodiment.

FIG. 6 is a block diagram illustrating an overall configuration of the biological information monitoring apparatus 1 according to the second embodiment. The biological information monitoring apparatus 1 of the first embodiment is provided with only one antenna 10 in principle, whereas the biological information monitoring apparatus 1 of the second embodiment is provided with at least two antennas including a transmission antenna (first antenna) 10 and a reception antenna (second antenna) 11.

As to configuration of the main body 20 (i.e., biological-information-monitoring main-body 20), the second embodiment is almost the same as the first embodiment, and the main body 20 in the second embodiment includes the RF signal generator 30, the transmission circuit 40, the coupling-amount detection circuit 50, and the displacement detection circuit 60.

The main body 20 in the second embodiment differs from the first embodiment in that the transmission circuit 20 in the second embodiment does not include the directional coupler (DC) 43. The power amplifier (PA) 42 of the transmission circuit 20 and the transmission antenna 10 are directly connected without passing through the directional coupler (DC) 43. The band-pass filter (BPF) 51 of the coupling-amount detection circuit 50 and the reception antenna 11 are also directly connected without passing through the directional coupler (DC) 43.

The coupling-amount detection circuit 50 of the second embodiment uses the signal-detection circuit 53 for detecting the transmitted signal, which is originally the high-frequency signal outputted from the RF signal generator 30, and is transmitted from the transmission antenna 10 through the object to the reception antenna 11, and detects the amount of near-field coupling on the basis of magnitude of the transmitted signal.

Considering that the power outputted from the transmission circuit 40 to the transmission antenna 10 is a constant value, the coupling-amount detection circuit 50 equivalently detects the S21 parameter indicating the insertion loss from the transmission antenna 10 to the reception antenna 11.

Figure 7B:
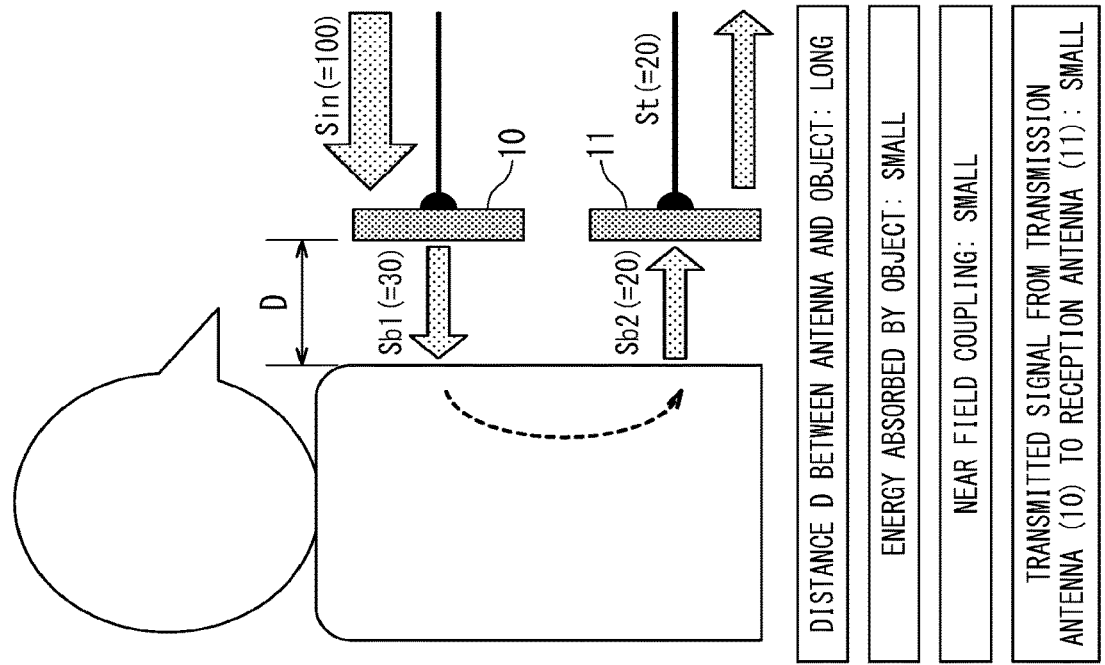
FIG. 7A and FIG. 7B are schematic diagrams illustrating the operation concept of the biological information monitoring apparatus according to the second embodiment.
Figure 7A:
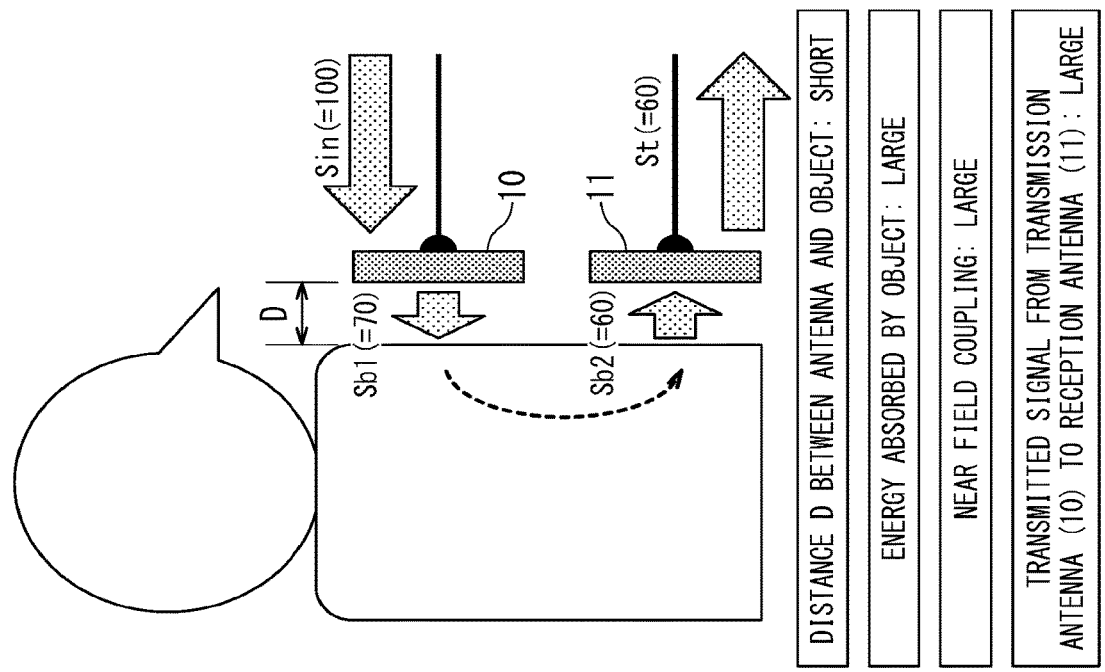

FIG. 7A and FIG. 7B are schematic diagrams illustrating the operation concept of the biological information monitoring apparatus 1 according to the second embodiment. FIG. 7A schematically illustrates the operation when the distance D between the object and the antenna 10 is short, while FIG. 7B schematically illustrates the operation when the distance D between the object and the antenna 10 is long. As mentioned above, the object (human body) has electrical conductivity. Thus, when the distance between the transmission antenna 10 and the object is short, the object (human body) more readily absorbs the energy from the transmission antenna 10. Hence, the energy absorbed from the transmission antenna 10 into the object increases. This means that the coupling amount of the near-field coupling between the object and the transmission antenna 10 is large.

Similarly, when the reception antenna 11 approaches the object, the energy inputted from the object to the reception antenna 11 also increases, and this means that the coupling amount of the near-field coupling between the object and the reception antenna 11 is large. The power Sin inputted to the antenna 10 is absorbed by the object as the power Sb1, propagates the interior and the surface of the object, and is transmitted to the reception antenna 11 as the power Sb2. When the distance D is short, the power Sb1 absorbed from the transmission antenna 10 to the object increases, and accordingly, the power Sb2 emitted from the object to the input antenna 11 increases. For example, when the power Sin inputted to the transmission antenna 10 is assumed to be 100, the power Sb absorbed by the object from the transmission antenna 10 may be 70, and the power Sb2 emitted from the object to the reception antenna 11 may be 60, and thus the power St exiting from the reception antenna 11 is also 60.

This means that the transmitted signal from the transmission antenna 10 to the reception antenna 11 increases and the insertion loss from the transmission antenna 10 to the reception antenna 11 decreases, when the distance D between the object and the transmission antenna 10/the reception antenna 11 is short. In other words, the S21 parameter (when expressed as an antilogarithm value), which is an index of the insertion loss from the transmission antenna 10 to the reception antenna 11, shows a large value.

On the other hand, as shown in FIG. 7B, when the distance D between the transmission antenna 10 and the object increases, the object becomes less likely to absorb the energy from the transmission antenna 10. Thus, the energy absorbed by the object from the transmission antenna 10 decreases. This means that the amount of near-field coupling between the object and the reception antenna 11 is reduced. Similarly, when the distance D between the reception antenna 11 and the object increases, the energy inputted from the object to the reception antenna 11 also decreases. This means that the amount of near-field coupling between the object and the reception antenna 11 is also reduced. For example, when the power Sin inputted to the transmission antenna 10 is assumed to be 100, the power Sb absorbed by the object from the transmission antenna 10 may become 30, and the power Sb2 emitted from the object to the reception antenna 11 may become 20, and thus, the power St exiting from the reception antenna 11 becomes also 20.

This means that the transmitted signal from the transmission antenna 10 to the reception antenna 11 decreases and the insertion loss from the transmission antenna 10 to the reception antenna 11 increases when the distance D between the object and the transmission antenna 10/the reception antenna 11 is long. In other words, the S21 parameter (when expressed as an antilogarithm value), which is an index of the insertion loss from the transmission antenna 10 to the reception antenna 11, shows a small value.

FIG. 8A is a graph for illustrating actually measured values of a transmitted signal from the transmission antenna 10 to the reception antenna 11. In this graph, the horizontal axis indicates time and the vertical axis indicates amplitude of the transmitted signal. The transmitted signal in the second embodiment is similar to the reflected signal (FIG. 3A) in the first embodiment and has a waveform in which a short-period fluctuation waveform corresponding to heartbeat is superimposed on a relatively long-period fluctuation waveform corresponding to respiration. This transmitted signal is also detected by the signal-detection circuit 53 of the coupling-amount detection circuit 50 and then is outputted to the displacement detection circuit 60.

The displacement detection circuit 60 performs filtering processing and/or Fourier transform processing on the reflected signal detected by the signal-detection circuit 53 so as to extract the respective two frequency components corresponding to the respiratory motion and heartbeat, and then generates a respiratory waveform shown in FIG. 8B and a heartbeat waveform shown in FIG. 8C in a manner similar to the first embodiment.

FIG. 9A to FIG. 9D are schematic diagrams illustrating disposition of the transmission antenna 10 and the reception antenna 11 used in the biological information monitoring apparatus 1 of the second embodiment. Many variations are conceivable for disposition and orientation of the transmission antenna 10 and the reception antenna 11 of the second embodiment. As a basic idea, the transmission antenna 10 and the reception antenna 11 are desirably disposed so as to sandwich the anatomical part where the body motion appears as much as possible. For example, in the case of detecting heartbeat, the transmission antenna 10 and the reception antenna 11 are desirably disposed so as to sandwich the heart in any one of the anterior-posterior direction, the right-left direction, and the head-foot direction of the object.

Figure 9A:
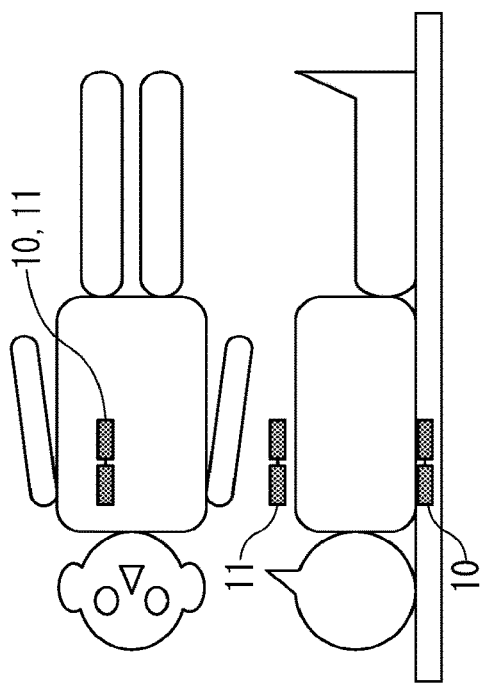
FIG. 9A to FIG. 9D are schematic diagrams illustrating disposition of the transmission antenna and the reception antenna to be used in the second embodiment.
Figure 9B:
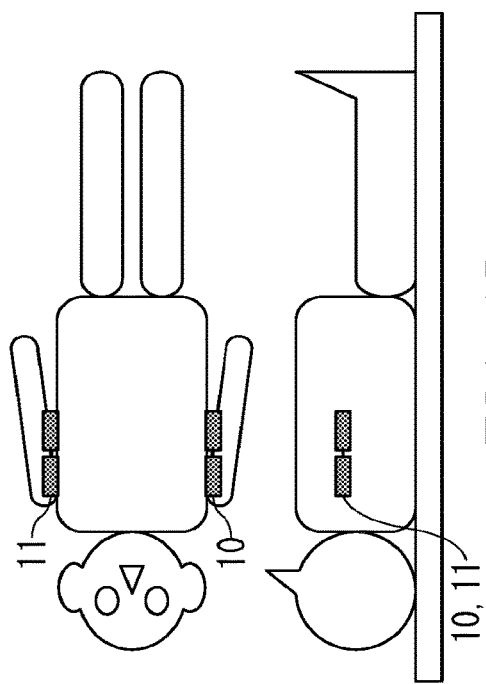
Figure 9C:
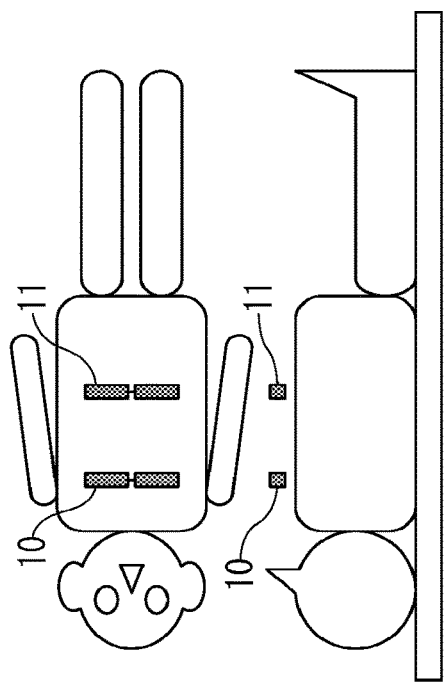
Figure 9D:
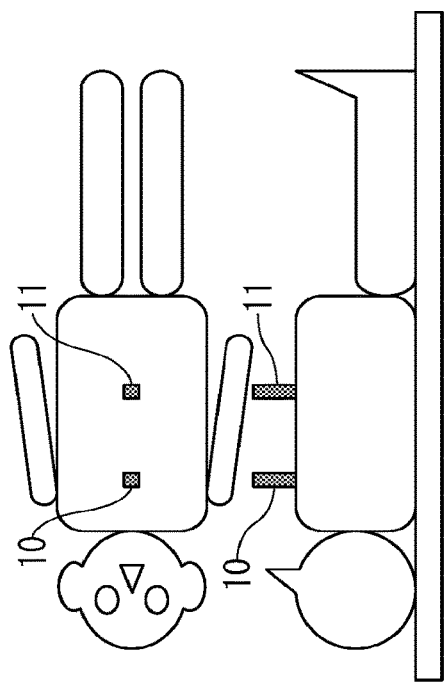

Each of FIG. 9A, FIG. 9B, and FIG. 9C illustrates a dipole antenna, and FIG. 9D illustrates a monopole antenna. FIG. 9A shows a disposition example in which the heart of the object is sandwiched between the transmission antenna 10 and the reception antenna 11 in the anterior-posterior direction.

FIG. 9B shows another disposition example in which the heart of the object is sandwiched between the transmission antenna 10 and the reception antenna 11 in the right-left direction.

FIG. 9C shows yet another disposition example in which the heart of the object is sandwiched between the transmission antenna 10 and the reception antenna 11 in the head-foot direction.

Meanwhile, FIG. 9D shows a disposition aspect in which the heart of the object is sandwiched between the transmission antenna 10 and the reception antenna 11, each of which is configured as a monopole antenna, in the head-foot direction.

Note that, there is no particular need to distinguish between the transmission antenna 10 and the reception antenna 11. In any of the disposition examples of FIG. 9A to FIG. 9D, the respective position of the transmission antenna 10 and reception antenna 11 can be interchanged.

The voltage standing wave ratio (VSWR) of the transmission antenna 10 used in the biological information monitoring apparatus 1 of the second embodiment is preferably set to, for example, a value between 2.0 and 5.0 similarly to the first embodiment. By contrast, as for the reception antenna 11, lower VSWR is preferred, for example, a VSWR of 2.0 or less is preferred.

Third Embodiment

Figure 10:
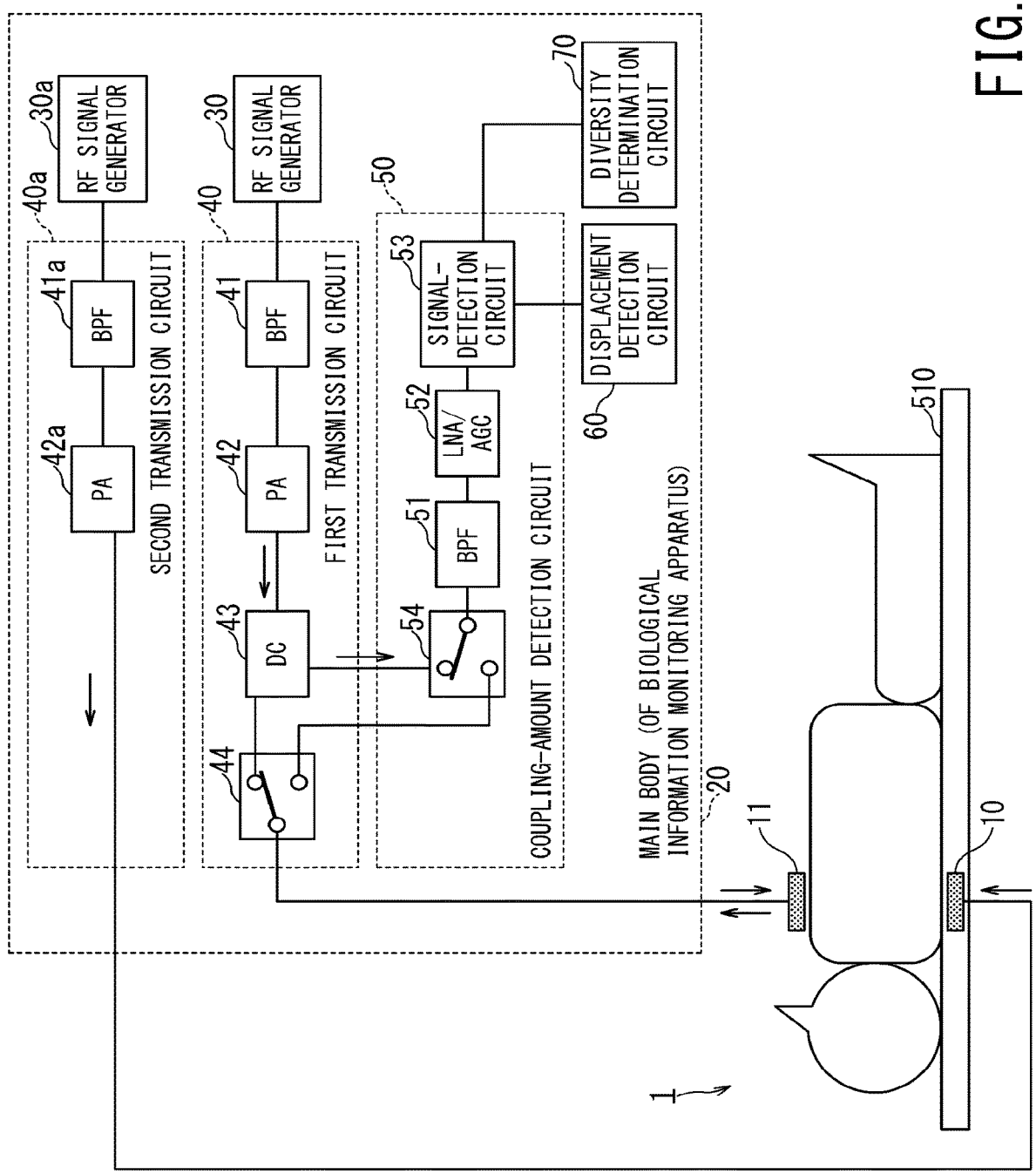
FIG. 10 is a block diagram illustrating an overall configuration of the biological information monitoring apparatus according to the third embodiment.

FIG. 10 is a configuration diagram illustrating an overall configuration of the biological information monitoring apparatus 1 according to the third embodiment. The biological information monitoring apparatus 1 of the third embodiment is a combination of the first embodiment and the second embodiment. Specifically, the third embodiment is configured to be able to select either one of the first mode corresponding to the first embodiment and the second mode corresponding to the second embodiment.

In the first mode, a high-frequency signal is inputted to the antenna 11, and the motion of the object such as heartbeat and/or respiration is measured on the basis of the reflected signal from the antenna 11, or on the basis of the S11 parameter of the antenna 11. In the second mode, a high-frequency signal is inputted to the antenna 10, and the motion of the object such as heartbeat and/or respiration is measured on the basis of the transmitted signal from the antenna 10 to the antenna 11, or on the basis of the S21 parameter from the antenna 10 to the antenna 11.

The RF signal generator 30 and the first transmission circuit 40 are configurations corresponding to the function for generating a high-frequency signal in the first mode. On the other hand, the RF signal generator 30a and the second transmission circuit 40a are configurations corresponding to the function for generating a high-frequency signal in the second mode. The coupling-amount detection circuit 50 is used in common in both of the first mode and the second mode.

The diversity determination circuit 70 monitors the reflected signal detected in the first mode and the transmitted signal detected in the second mode, and selects either one of the first mode and the second mode. When monitoring the reflected signal in the first mode, the diversity determination circuit 70 switches both of the switch 44 of the first transmission circuit 40 and the switch 54 of the coupling-amount detection circuit 50 to the side of the directional coupler 43 as shown in the state of FIG. 10. When monitoring the transmitted signal in the second mode, the diversity determination circuit 70 switches the switches 44 and 54 to the opposite sides of the state shown in FIG. 10.

The diversity determination circuit 70 compares the fluctuation range (i.e., amplitude of fluctuations) of the reflected signal in the first mode with the fluctuation range of the transmitted signal in the second mode, and selects the mode having the larger fluctuation range. For example, when it is determined that the monitored fluctuation range of the reflected signal is larger than the monitored fluctuation range of the transmitted signal, the diversity determination circuit 70 selects the first mode. Alternatively, the diversity determination circuit 70 may individually perform Fourier transform on the reflected signal and the transmitted signal, and then may select the mode in which the frequency component corresponding to the heartbeat is larger, or may select the mode in which the frequency component corresponding to the respiration is larger.

After selecting either one of the first mode and the second mode, the diversity determination circuit 70 sets and fixes the switches 44 and 54 to the state corresponding to the selected mode, then measures either one of the reflected signal and transmitted signal under the selected mode, and then detects the body motion signal such as heartbeat and a respiratory motion.

Modification of Third Embodiment

The biological information monitoring apparatus 1 of the modification of the third embodiment performs diversity processing by using two or more antennas 10 and 11. In this diversity processing, one antenna that detects the body motion signal with maximum sensitivity is selected or a combination of two or more antennas that can detect the body motion signal with maximum sensitivity is selected.

Figure 11A:
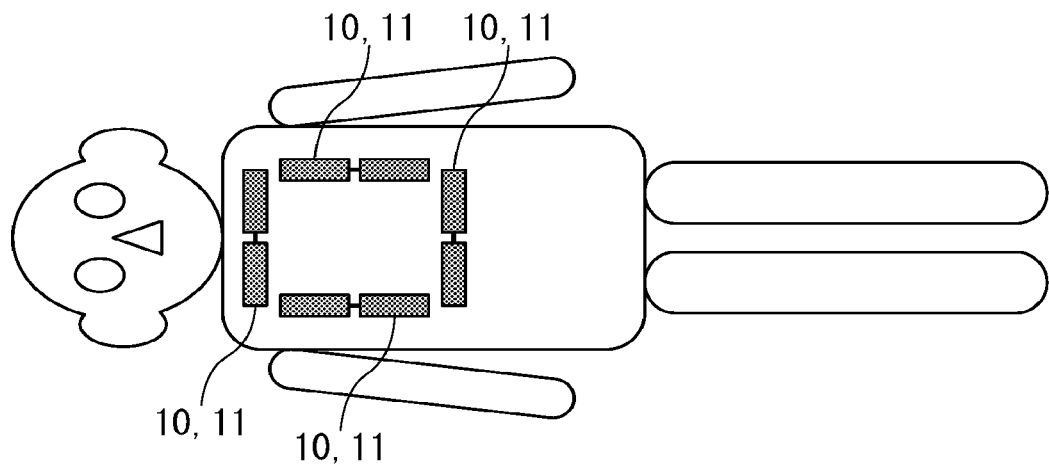
FIG. 11A and FIG. 11B are schematic diagrams illustrating disposition of four antennas for performing diversity processing.
Figure 11B:
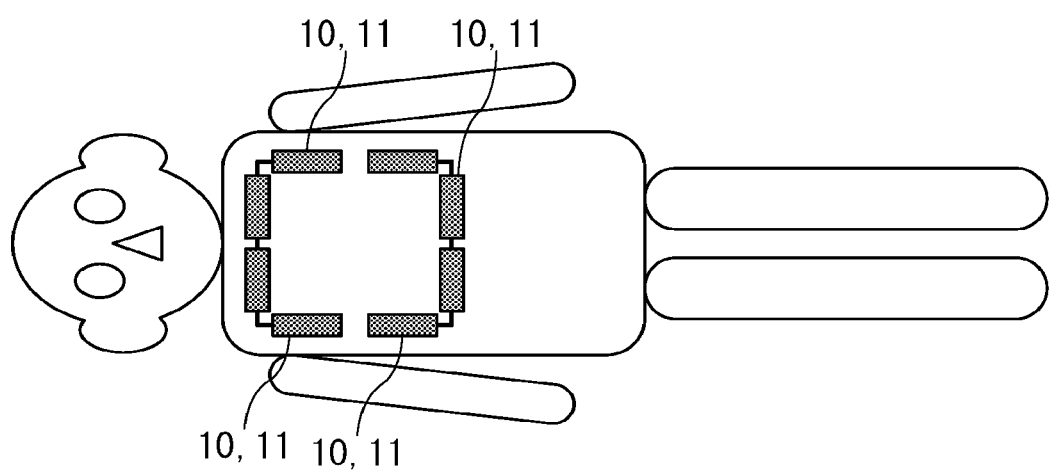

FIG. 11A and FIG. 11B are schematic diagrams illustrating disposition of four antennas for performing the diversity processing. In this case, for example, as shown in FIG. 11A, four dipole antennas 10 and 11 may be disposed so as to surround the heart. Further, as shown in FIG. 11B, the antennas 10 and 11, in each of which the dipole antenna is bent at a substantially right angle at the center, may be disposed so as to surround the heart.

In the case of performing the diversity processing by using the biological information monitoring apparatus 1 of the first embodiment, or in the case of performing the diversity processing in the first mode of the third embodiment, one antenna that can detect the body motion signal with maximum sensitivity is selected among the four antennas.

Alternatively, in the case of performing the diversity processing by using the biological information monitoring apparatus 1 of the second embodiment, or in the case of performing the diversity processing in the second mode of the third embodiment, for example, one antenna is selected as a transmission antenna 10, and further, one antenna capable of detecting the body motion signal with maximum sensitivity is selected among the remaining three antennas as a reception antennas 11, or synthetic antenna processing is performed by using an arbitrary combination of the remaining three antennas, causing a synthesized reception antenna 11.

In the modification of the third embodiment, for example, a circuit having a function similar to that of the diversity circuit 70 shown in FIG. 10 may be provided so that this circuit performs the above-described antenna-selection processing and/or synthetic antenna processing.

(MRI Apparatus)

Figure 12:
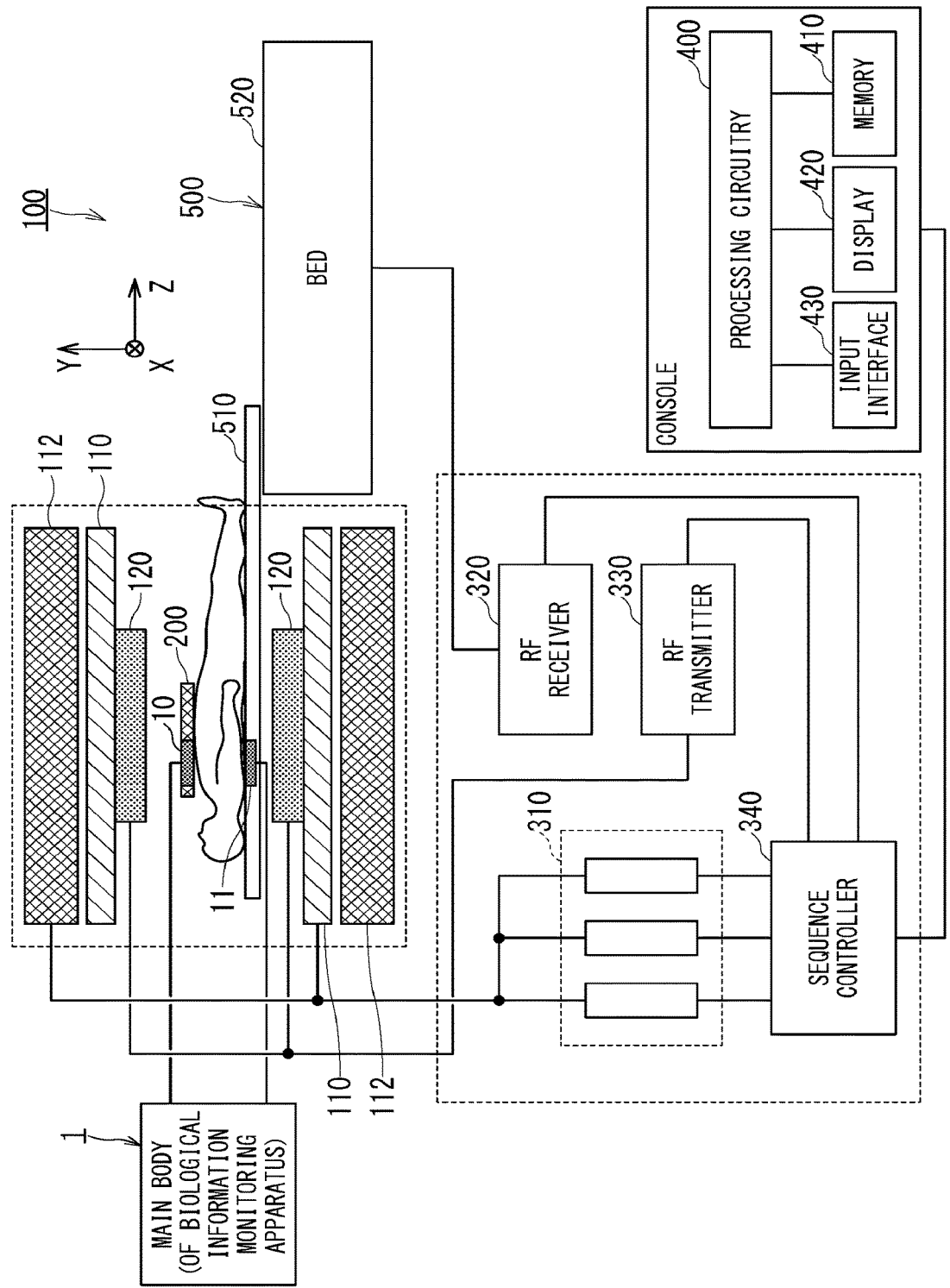
FIG. 12 is a configuration diagram illustrating an MRI apparatus that is provided with the biological information monitoring apparatus according each embodiment.

FIG. 12 is a configuration diagram illustrating an MRI apparatus 100 that is provided with the biological information monitoring apparatus 1 according each embodiment described above.

The MRI apparatus 100 includes a static magnetic field magnet 112, a gradient coil 110, and a whole body (WB) coil 120, and these components are housed in a cylindrical housing. The MRI apparatus 100 also includes: a bed 500 provided with a bed body 520 and a table 510; and at least one RF coil 200 disposed close to the object. The RF coil 200 is also referred to as a local coil or surface coil.

The MRI apparatus 100 further includes a gradient coil power supply 310, an RF receiver 320, an RF transmitter 330, and a sequence controller 340. The MRI apparatus 100 further includes a console, i.e., a computer that is provided with processing circuitry 400, a memory 410, a display 420, and an input interface 430.

The biological information monitoring apparatus 1 includes the antennas 10 and 11 in addition to the main body 20 shown in FIG. 1, FIG. 6, and FIG. 10. The antennas 10 and 11 are disposed close to the object but are not required to be directly attached to the skin of the object. Although the antennas 10 and 11 may be individually disposed in the vicinity of the object, the antennas 10 and 11 may be embedded in the RF coil 200 as shown in FIG. 12 or may be embedded in the table 510.

Figures 13A, 13B:
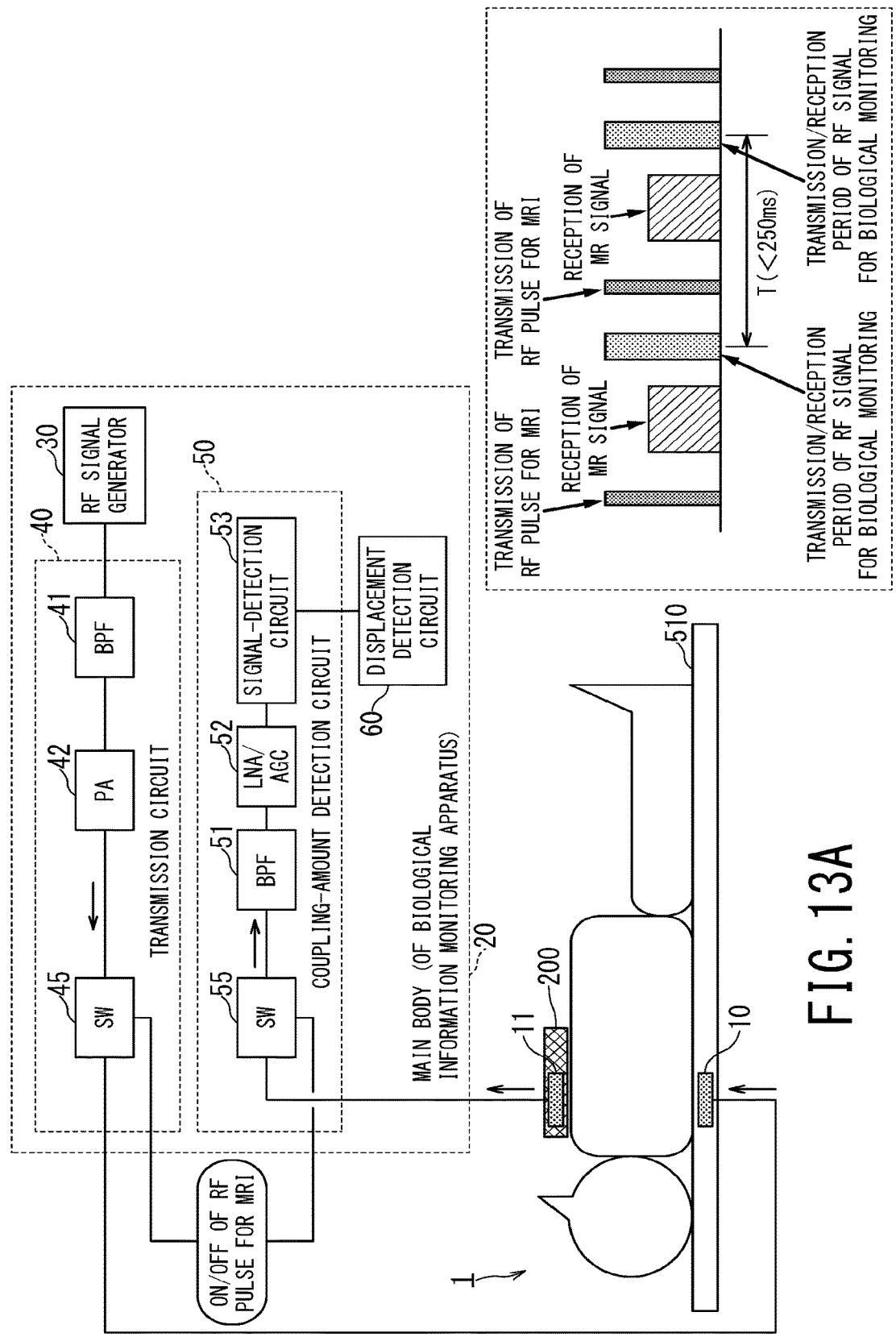
FIG. 13A is a block diagram illustrating a configuration of the biological information monitoring apparatus to be used in the MRI apparatus.
FIG. 13B is a schematic diagram illustrating a transmission/reception period of a high-frequency signal for a biological monitor.

FIG. 13A is a block diagram illustrating a configuration of the biological information monitoring apparatus 1, which is used in the MRI apparatus 100. Although the MRI apparatus 100 can be used along with any of the above-described embodiments, FIG. 13A illustrates the biological information monitoring apparatus 1 of the second embodiment. In the MRI apparatus 100, the RF transmitter 330 outputs an RF pulse for causing magnetic resonance with very high power, and the RF pulse is emitted from the WB coil 120 toward the object. With this emission, very large RF power is inputted to the main body 20 of the biological information monitoring apparatus 1 via the antennas 10 and 11.

Thus, in the biological information monitoring apparatus 1 used in the MRI apparatus 100, the protection switches 45 and 55 are respectively provided at the output terminal of the transmission circuit 40 and the input terminal of the coupling-amount detection circuit 50. The protection switches 45 and 55 are turned on and off by using a control signal sent from the main body of the MRI apparatus 100.

FIG. 13B is a schematic diagram illustrating a transmission/reception period of a high-frequency signal for biological monitoring. As shown in FIG. 13B, in order to avoid interference between the MRI apparatus 100 and the biological information monitoring apparatus 1, the high-frequency signal for biological monitoring is transmitted and received during a period excluding the transmission period of each RF pulse for causing magnetic resonance and the reception period of each MR signal.

The repetition period T of the transmission/reception period of the high-frequency signal for biological monitoring can be defined from the period of heartbeat and/or the period of respiration. The frequency of heartbeat can be assumed to be approximately 2 Hz or less, and the frequency of respiration can be assumed to be approximately 0.5 Hz or less. From the view point of the sampling theorem, when sampling is performed at twice the higher frequency, i.e., at a frequency of 4 Hz or higher, the waveform of the heartbeat and the waveform of the respiration can be accurately extracted. Thus, the repetition period T may be set to 250 ms (=1/(4 Hz)) or less.

It is preferred that the frequency of the high-frequency signal for biological monitoring is higher than the Larmor frequency used for the MRI apparatus 100. When the frequency of the high-frequency signal for biological monitoring is set to be higher than the Larmor frequency, not only the high frequency signal itself for biological monitoring but also its harmonics can be prevented from entering the reception band of MR signal of the MRI apparatus 100.

Figure 14A:
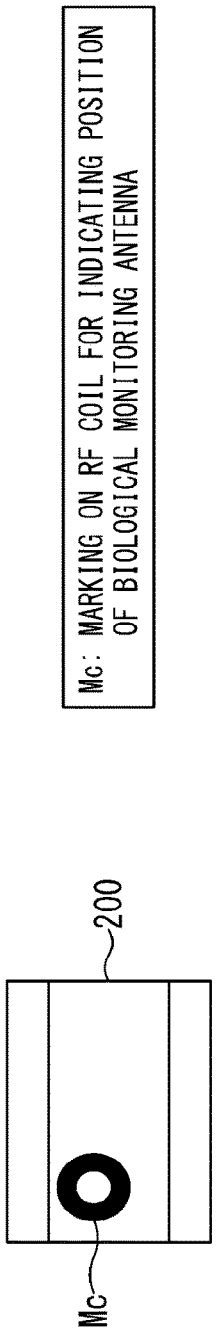
FIG. 14A is a schematic diagram illustrating marking that is performed on the RF coil to indicate the position of the antenna.
Figure 14B:
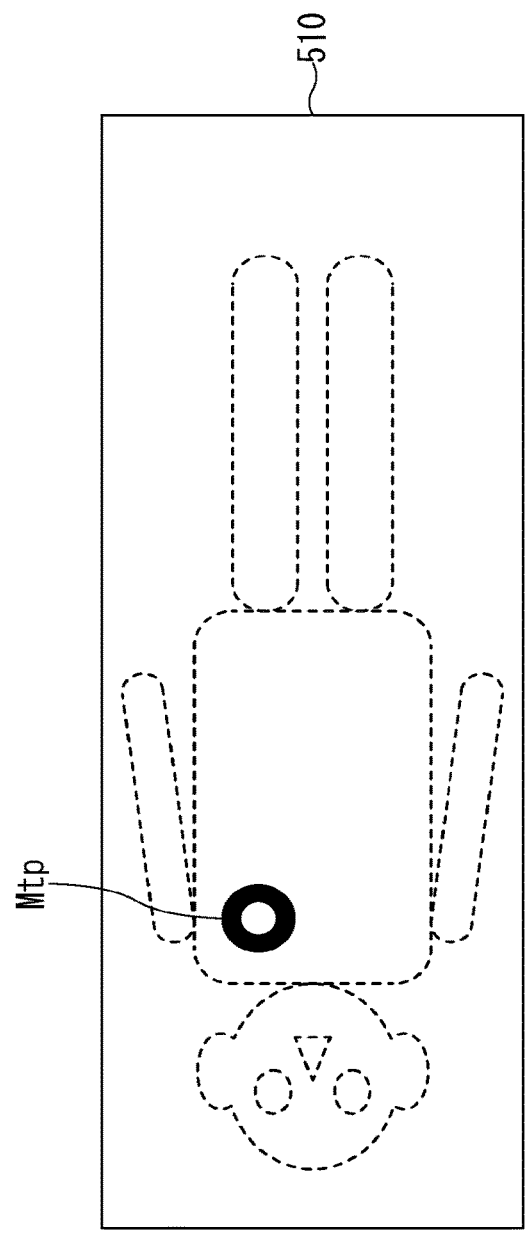
FIG. 14B is a schematic diagram illustrating marking that is performed on the table to indicate the position of the antenna.

FIG. 14A is a schematic diagram illustrating marking that is performed on the RF coil 200 to indicate the position of the antennas 10 and 11, and FIG. 14B is a schematic diagram illustrating marking that is performed on the table 510 to indicate the position of the antennas 10 and 11. As described above, the antennas 10 and 11 of the biological information monitoring apparatus 1 can be mounted by being embedded in the RF coil 200 or the table 510 of the bed 500. In the case of measuring heartbeat, it is preferred that the antennas 10 and 11 are disposed near the heart of the object. Thus, marking is preferably provided such that a user can readily and visually recognize the antennas 10 and 11 embedded in the RF coil 200 and/or table 510, and further, the respective positions of the object and the RF coil 200 are preferably adjusted such that this marking is near the heart of the object.

(Frequency of Radio Signal for Biological Information Monitoring Apparatus)

As described above, the frequency of radio signal used for the biological information monitoring apparatus 1 is preferably higher than the Larmor frequency used for the MRI apparatus 100. Hereinafter, the frequency of the radio signal used by the biological information monitoring device 1 will be described in detail.

As described above, the biological information monitoring apparatus 1 detects the amount of near-field coupling caused by an electric field between the object and the antenna 10 of the biological information monitoring apparatus 1, and detects physical displacement of the object on the basis of change in amount of near-field coupling. Here, one of the typical examples of the physical displacement of the object is heartbeat of the object.

The inventors, thus, have sought to determine the frequency used by the biological information monitoring apparatus 1 from the viewpoint with what frequency the heartbeat of the object can be detected with high sensitivity. The inventors further have obtained the idea that the frequency at which the heartbeat can be detected with high sensitivity should be the frequency corresponding to the resonance length of the heart in the body of the object (i.e., resonance frequency). Then, the present inventors have performed experiments for confirming the idea, and obtained an experimental result that affirms the idea.

Figure 15:
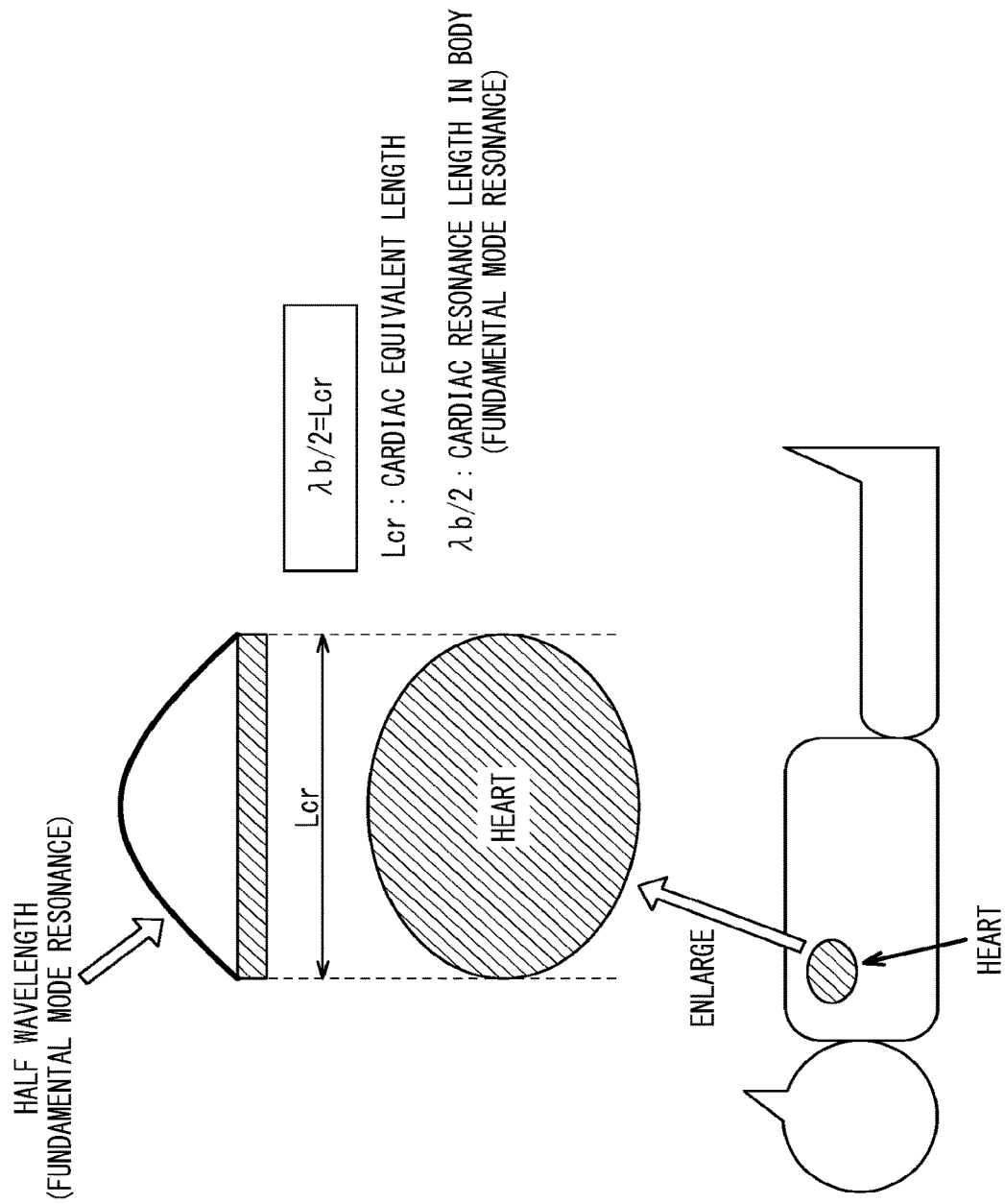
FIG. 15 is a schematic diagram illustrating the basic concept in the case of determining the frequency to be used by the biological information monitoring apparatus.

FIG. 15 is a schematic diagram illustrating the basic concept for determining the frequency used by the biological information monitoring apparatus 1. As shown in FIG. 15, the size of the heart of the object, for example, the length of the heart in the head-foot direction is assumed to be the cardiac equivalent length Lcr. In this case, half of the wavelength λb of the resonance frequency for the cardiac equivalent length Lcr is (i.e., λb/2 is) the resonance length of the heart in the body of the object. The resonance length here corresponds to the fundamental mode resonance, and the equivalent length Lcr and the wavelength λb are related by Lcr=λb/2.

For the same cardiac equivalent length Lcr (i.e., the same heart size), there can be nth order resonance modes. In this case, the cardiac equivalent length Lcr and the wavelength λb of the nth-order resonance modes are related by Expression 1 below.

$$Lcr = (n) \cdot \lambda b / 2 \qquad \text{Expression 1}$$

In other words, the higher the order "n" of the resonance mode, the shorter the wavelength λb, at which resonance occurs, becomes, and the higher the resonance frequency which is the reciprocal of this resonance wavelength λb, becomes. The wavelength λb inside the body of the object is shorter than the wavelength λ outside the body (i.e., the wavelength λ in the air). When the relative permittivity in the body is represented by εr (>1), the wavelength λb in the body is expressed by Expression 2 below.

$$\lambda b = \lambda \cdot (1/\sqrt{\varepsilon r}) \qquad \text{Expression 2}$$

$(1/\sqrt{\varepsilon r})$ is an index that is generally called a wavelength shortening rate or shortening coefficient of wavelength. Since the frequency f and the wavelength λ in the air have a relationship of f=c/λ (c is the speed of light), Expressions 1 and 2 establish the relation of Expression 3 between the resonance frequency fn in the nth-order resonance modes and the cardiac equivalent length Lcr.

$$fn = c/\lambda = c/(\lambda b \cdot \sqrt{\varepsilon r}) = n \cdot c/(2 Lcr \sqrt{\varepsilon r}) \qquad \text{Expression 3}$$

Here, it is assumed that the relative permittivity εr of the human body can be approximated by the relative permittivity of fat, and the relative permittivity εr of fat is assumed to be εr=11. If the unit of the resonance frequency is MHz and the unit of the cardiac equivalent length Lcr is cm (centimeter), Expression 3 is expressed by Expression 4 below.

$$fn(\text{MHz}) = n \cdot (4520)/Lcr \text{ (cm)} \qquad \text{Expression 4}$$

Thus, the resonance frequency f1 at the fundamental mode resonance (n=1) and the resonance frequency f2 at the double mode resonance (n=2) are respectively expressed by Expressions 5 and 6 below.

$f1(MHz)=(4520)/Lcr$ (cm) Expression 5 (for fundamental mode resonance)

$f2(MHz)=(9040)/Lcr$ (cm) Expression 6 (for double mode resonance}

It is said that size of the heart of an adult is about 9 to 11 cm in the horizontal direction (i.e., right-left direction of the object) and about 12 to 15 cm in the vertical direction (head-foot direction of the object). Accordingly, if the cardiac equivalent length Lcr in Expressions 5 and 6 is assumed to be 14 cm, the resonance frequency f1 in the fundamental mode resonance is 322 MHz, while the resonance frequency f2 in the double mode resonance is 644 MHz.

The present inventors conducted an experiment in which the frequency of the biological information monitoring apparatus 1 was changed from about 300 MHz to about 650 MHz to search for the frequency at which the heartbeat was more stably and clearly detected. In this experiment, the return loss (S11 parameter) was measured by using the configuration of the first embodiment shown in FIG. 1.

Figure 16:
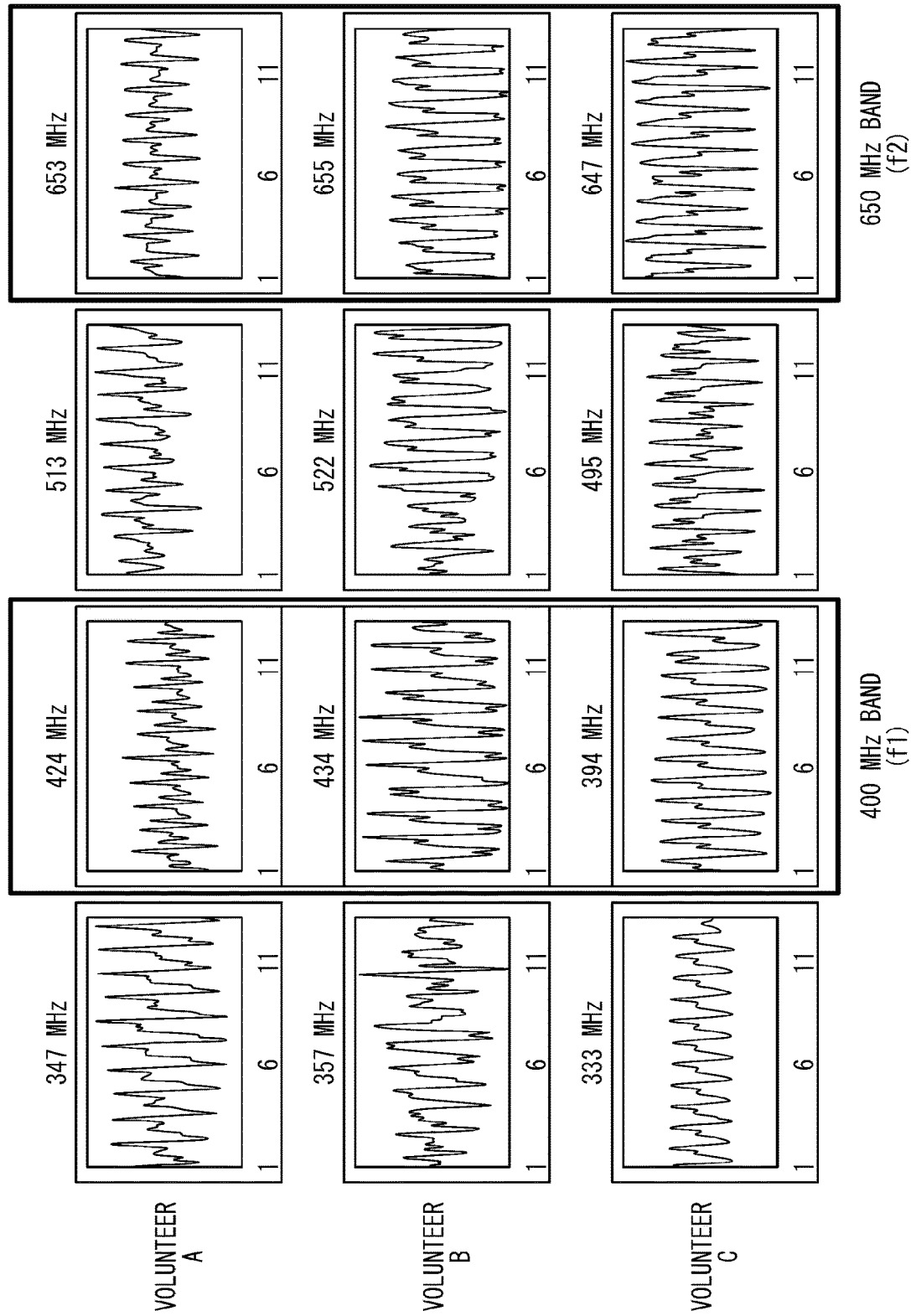
FIG. 16 is a graph of results of an experiment for searching for a frequency at which heartbeat is more stably and clearly detected.

FIG. 16 is a diagram showing results of the experiment as twelve graphs. The horizontal axis of each graph indicates time, and the numbers on the horizontal axis correspond to seconds. The vertical axis of each graph indicates the value of the S11 parameter expressed as a relative value. It is clear that the fluctuation cycle of the S11 parameter is about a little over 1 second and corresponds to the heartbeat cycle.

In this experiment, for three objects (persons) including volunteers A, B, and C, measurement was performed by using four antennas having different reference frequencies (respective four antennas for 300 MHz, 400 MHz, 500 MHz, and 600 MHz). In the leftmost column of FIG. 16, the three graphs for the respective volunteers A, B, and C show the measured frequency at which change in S11 parameter appears most remarkably in the vicinity of 300 MHz, and these graphs were obtained by using the antenna for 300 MHz and finely adjusting its frequency near 300 MHz. The frequency shown at the top of each graph indicates the frequency after fine adjustment. Similarly, the second leftmost column in FIG. 16 shows the result of measurement by using the antenna for 400 MHz, the third leftmost column in FIG. 16 shows the result of measurement by using the antenna for 500 MHz, and the rightmost column in FIG. 16 shows the result of measurement by using the antenna for 600 MHz.

Although change in S11 parameter corresponding to heartbeat can be read in any of the measurement results, in the 300 MHz band in the leftmost column and the 500 MHz band in the third leftmost column, some measurement results have waveform disturbances (for example, waveform distortions in the measurement results of the volunteer B in the 300 MHz band and 500 MHz band). Also, in the measurement result of volunteer C in the 300 MHz band, the fluctuation amplitude of the S11 parameter is clearly smaller than in other frequency bands.

By contrast, in the 400 MHz band and the 650 MHz band, change in S11 parameter is relatively stable for any volunteer. In the 400 MHz band and the 650 MHz band, particularly for the volunteers B and C, satisfactory measurement results were obtained in which the fluctuation amplitude was large and the fluctuation amplitude was almost constant during the measurement period.

From these experimental results, in the biological information monitoring apparatus 1, it is considered that the 400 MHz band and the 650 MHz band are suitable as the frequencies to be used for detecting heartbeat.

As described above, the present inventors conducted the above-described experiment under the idea that the frequency at which heartbeat can be detected with high sensitivity will be the frequency corresponding to the cardiac equivalent length in the body of the object (i.e., resonance frequency).

Figure 17:
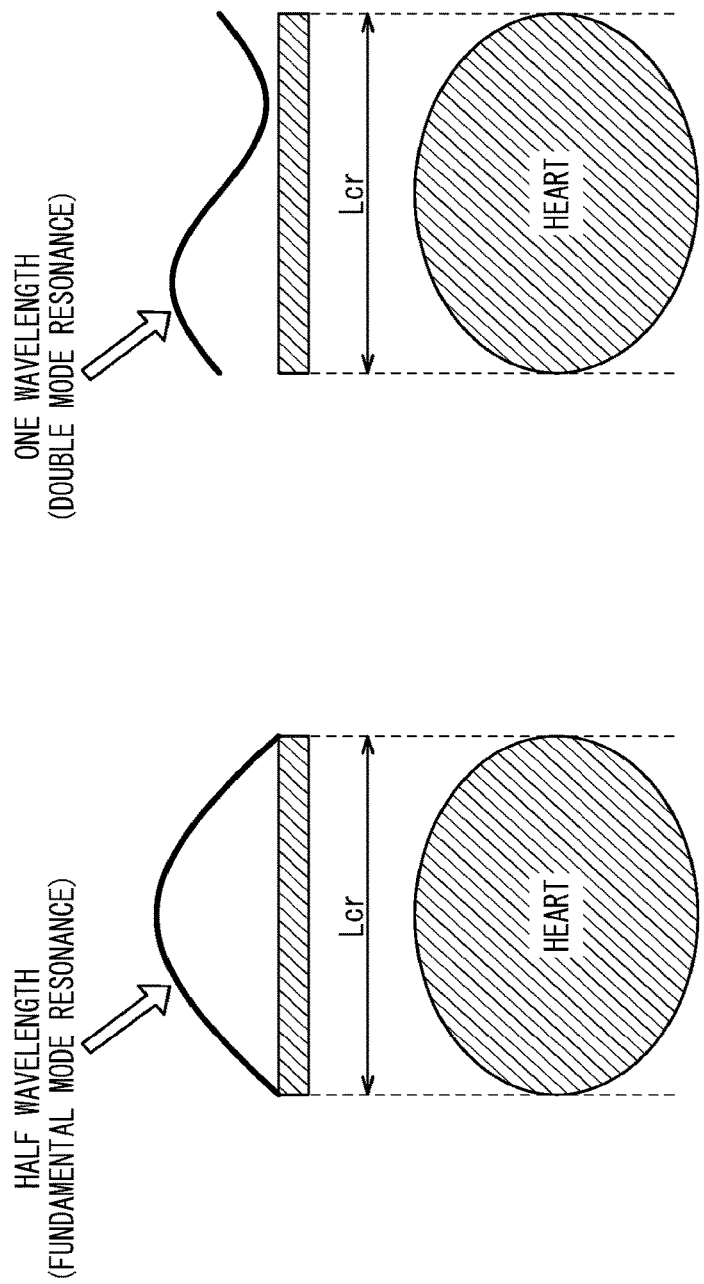
FIG. 17 is a schematic diagram for verifying an idea for determining the frequency to be used by the biological information monitoring apparatus and its experimental result.

FIG. 17 is a schematic diagram for verifying the above-described experimental results and the idea of the present inventors.

When the 400 MHz band is applied as the first preferred frequency obtained from the experimental results to Expression 5 corresponding to the fundamental mode resonance, the cardiac equivalent length Lcr (=cardiac resonance length $\lambda b/2$ in the fundamental mode resonance) becomes 11.3 cm. This size is considered to be in a range that does not contradict the size of the heart of an adult described above.

On the other hand, when the 650 MHz band is applied as the second preferred frequency obtained from the experimental results to Expression 6 corresponding to the double mode resonance, the cardiac equivalent length Lcr (=cardiac resonance length $\lambda b/2$ in the double mode resonance) becomes 13.9 cm. This size is also considered to be in a range that does not contradict the size of the heart of an adult described above.

In the biological information monitoring apparatus 1 of the above-described embodiments, it is considered preferable to use a high-frequency signal, frequency of which is the resonance frequency corresponding to the cardiac equivalent length in the body of the object. Further, it is considered more preferable to use a high-frequency signal having one or half wavelength equal to the equivalent length of the heart of the object. Hereinafter, the (resonance) frequency having a half wavelength equal to the cardiac equivalent length is denoted as the fundamental mode frequency f1, and the (resonance) frequency having one wavelength equal to the cardiac equivalent length is denoted as the double mode frequency f2.

FIG. 18A to FIG. 18C, FIG. 19A, and FIG. 19B are configuration diagrams illustrating various types of antennas and RF signal generators used in the biological information monitoring apparatus 1 of the present embodiment.

Figure 18C:
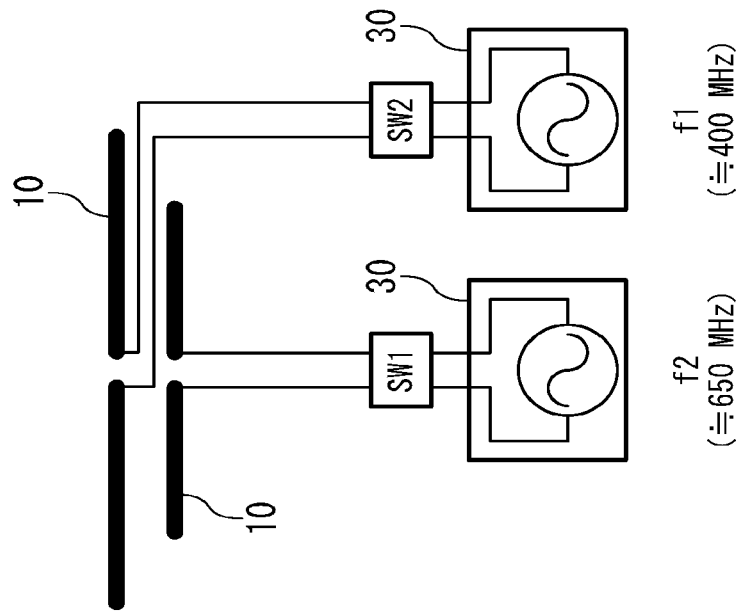
FIG. 18A to FIG. 18C are configuration diagrams illustrating various antennas and RF signal generators to be used by the biological information monitoring apparatus of one embodiment.
Figure 18B:
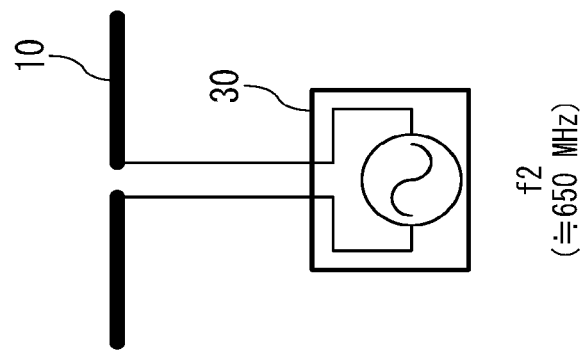
Figure 18A:
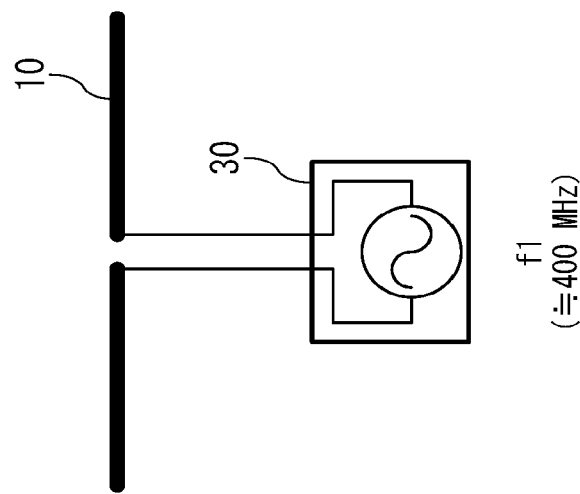
Figure 19A:
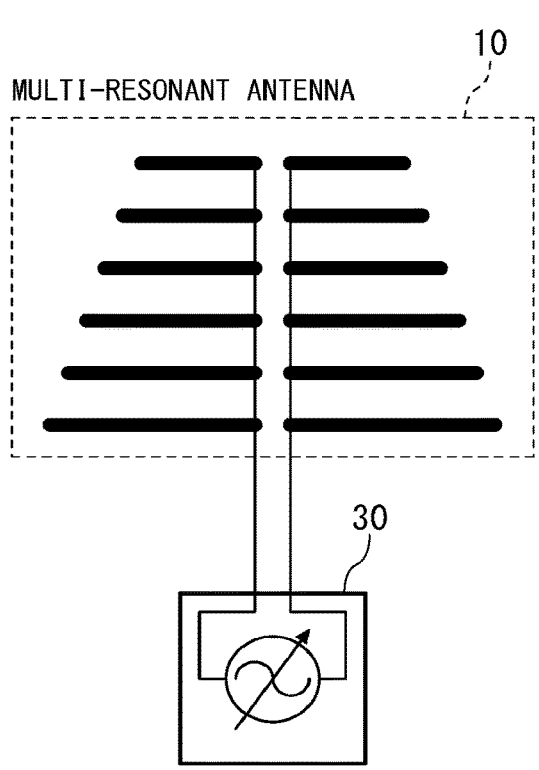
FIG. 19A and FIG. 19B are configuration diagrams illustrating other antennas and RF signal generators to be used by the biological information monitoring apparatus of one embodiment.
Figure 19B:
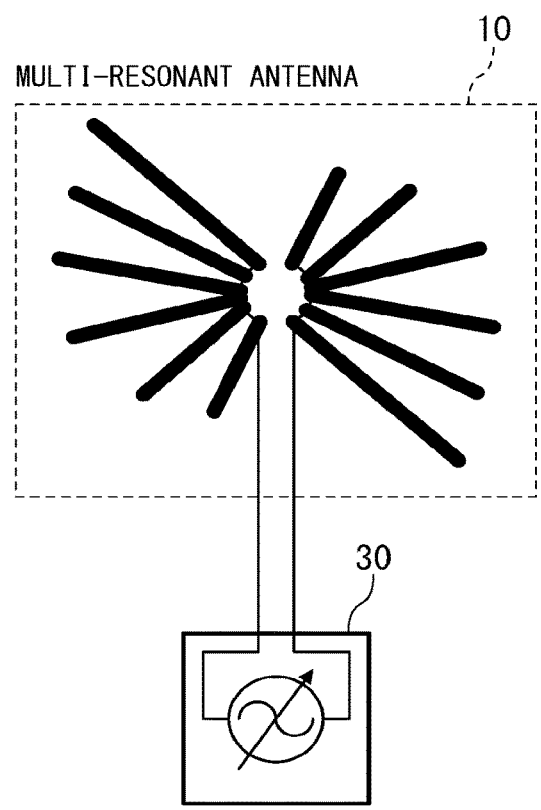

FIG. 18A shows an RF signal generator 30 configured to generate a high-frequency signal of the fundamental mode frequency f1 (for example, about 400 MHz) with respect to the cardiac size, and the antenna 10 (for example, a half-wave dipole antenna) configured to resonate at the fundamental mode frequency f1.

FIG. 18B shows another RF signal generator 30 configured to generate a high-frequency signal of the double mode frequency f2 (for example, about 650 MHz) with respect to the cardiac size, and the antenna 10 (for example, a half-wave dipole antenna) that resonates at the double mode frequency f2.

FIG. 18C illustrates a configuration that includes a RF signal generator 30 of f1 in FIG. 18A, another RF signal generator 30 of f2 in FIG. 18B, a first antenna 10 configured to resonate at the fundamental mode frequency f1, another second antenna 10 configured to resonate at the double mode frequency f2, and switches SW1 and SW2 for selecting one of the high-frequency signal having the fundamental mode frequency f1 and the high-frequency signal having the double mode frequency f2. As to which signal is selected from the high-frequency signal of the fundamental mode frequency f1 and the high-frequency signal of the double mode frequency f2, it is based on, for example, results of the measurement performed beforehand. For example, the high-frequency signal having a larger fluctuation amplitude of the S11 parameter is selected from the two choices.

In the configurations shown in FIG. 18A to FIG. 18C, some modifications are conceivable. For example, in each configuration shown in FIG. 18A to FIG. 18C, the RF signal generator 30 may generate a high-frequency signal having a half wavelength that is equal to or smaller than the size of the heart of the object. In other words, the RF signal generator 30 may generate a high-frequency signal, frequency of which matches the (resonant) frequency of a higher-order mode than the fundamental mode.

As described above, the size of the heart varies among individuals even in adults, and thus, the resonance frequency for the heart slightly varies among individuals. For this reason, each of the antennas shown in FIG. 18A to FIG. 18C may be configured as a wideband antenna having a frequency bandwidth that covers a variation range of the resonance frequency according to the variation in size of the heart between individuals.

Additionally, in each configuration shown in FIG. 18A to FIG. 18C, the RF signal generator 30 may be configured to have a function of sweeping the frequency of high-frequency signals so as to cover the variation range of the resonance frequency according to the variation in size of the heart between individuals.

When the size of the heart is significantly different, such as between adults and young children, the resonance frequency corresponding to the cardiac equivalent length is also significantly different, and thus the single resonance type antenna shown in FIG. 18A to FIG. 18C may be unable to cover both resonance frequencies in some cases.

In such cases, it is preferred to use the configuration including a multi-resonant antenna 10 and a variable-frequency RF signal generator 30, as illustrated in FIG. 19. The multi-resonant antenna 10 is configured as, for example, an antenna including a plurality of elements that are different in length from each other so as to correspond to respective resonance frequencies. The cardiac size varies from object to object, for example, the cardiac size differs significantly between young children and adults. Even if the cardiac equivalent length of a specific object is significantly different from a standard value of the cardiac equivalent length, the above-described configuration enables the biological information monitoring apparatus 1 to select an appropriate frequency to be used by the multi-resonant antenna 10 and the variable-frequency RF signal generator 30, depending on the cardiac size of the specific object.

In other words, this configuration enables the biological information monitoring apparatus 1 to select the above-described appropriate frequency regardless of variations in cardiac equivalent length between individuals in adults and variations in orientation of the heart at the time of measurement.

Furthermore, the configuration having the multi-resonant antenna 10 and the variable frequency RF signal generator 30 shown in FIG. 19 can use a high-frequency signal having a frequency that avoids mutual interference with MR signals. Even if one of the fundamental mode frequency f1 and the double mode frequency f2 interferes with the Larmor frequency of the MRI apparatus 1, the configuration shown in FIG. 19 can select the frequency having no mutual interference from the fundamental mode frequency f1 and the double mode frequency f2.

So far, from the viewpoint of detecting the heartbeat satisfactorily, the frequency to be used by the biological information monitoring apparatus 1 is selected and the antenna configuration corresponding to this selected frequency have been described by referring to FIG. 15 to FIG. 19.

In the following, a description will be given of an antenna configuration that can detect heartbeat satisfactorily, while sufficiently suppressing respiratory motions, by referring to FIG. 20 and FIG. 21.

Figure 20A:
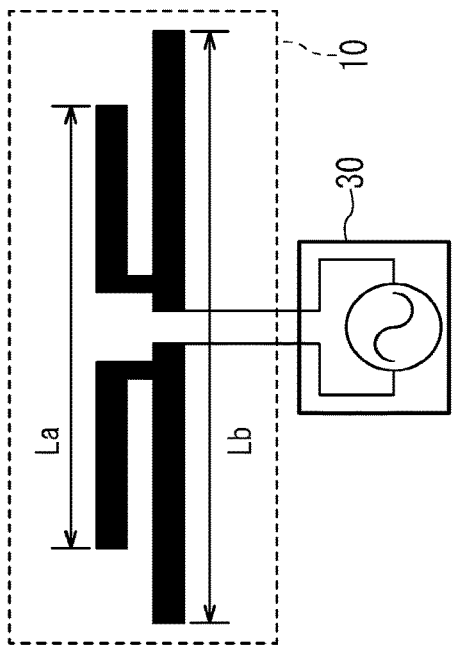
FIG. 20A is a configuration diagram illustrating a multi-element antenna of one embodiment.
Figure 20C:
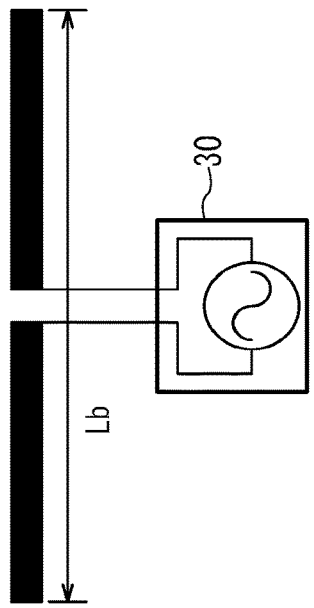
FIG. 20C is a configuration diagram illustrating a conventional dipole antenna.
Figure 20B:
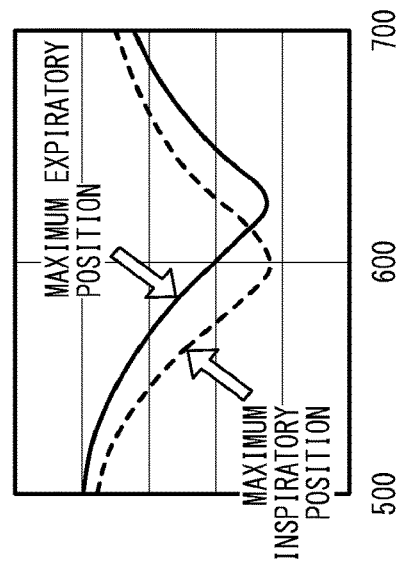
FIG. 20B is a frequency characteristic graph of the S11 parameter of the multi-element antenna shown in FIG. 20A.

FIG. 20A is a configuration diagram illustrating a multi-element antenna according to the present embodiment, and FIG. 20B is a frequency characteristic graph of the S11 parameter corresponding to the configuration of FIG. 20A. The multi-element antenna shown in FIG. 20A is configured as an antenna obtained by combining two dipole antennas that are different in length. For example, one of the two dipole antennas has a length Lb corresponding to 600 MHz, and the other of the two dipole antennas has a different length La (for example, La=0.8 Lb)

Figure 20D:
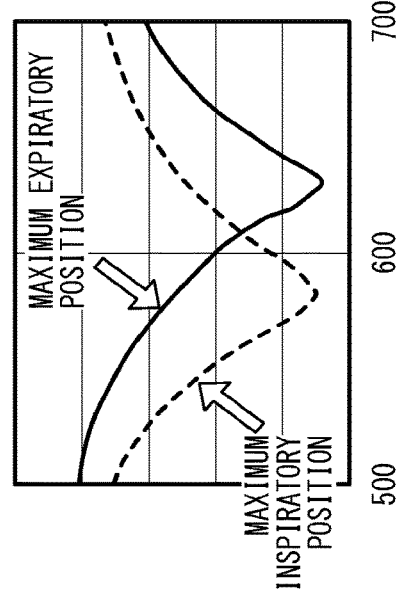
FIG. 20D is a frequency characteristic graph of the S11 parameter of the dipole antenna shown in FIG. 20C.

FIG. 20C is a configuration diagram illustrating a conventional dipole antenna as a comparative example, and FIG. 20D is a frequency characteristic graph of the S11 parameter corresponding to the configuration of FIG. 20C.

In each of the two graphs, the horizontal axis indicates the frequency (MHz) and the vertical axis indicates the value of the S11 parameter shown as a relative value. In each of the two graphs, the solid line indicates the value of the S11 parameter at the maximum expiratory position (i.e., in the state where the object expires (or exhales) to the maximum), and the broken line indicates the S11 parameter in the maximum inspiratory position (i.e., in the state where the object inspires (or inhales) to the maximum).

As is clear from the two graphs, the difference in value of the S11 parameter between the maximum expiratory position and the maximum inspiratory position (i.e., difference between the solid line and the broken line at the same frequency) is smaller in the multi-element antenna than in the conventional dipole antenna. This means that the multi-element antenna is less susceptible to respiratory motions than the conventional dipole antenna.

Figure 21:
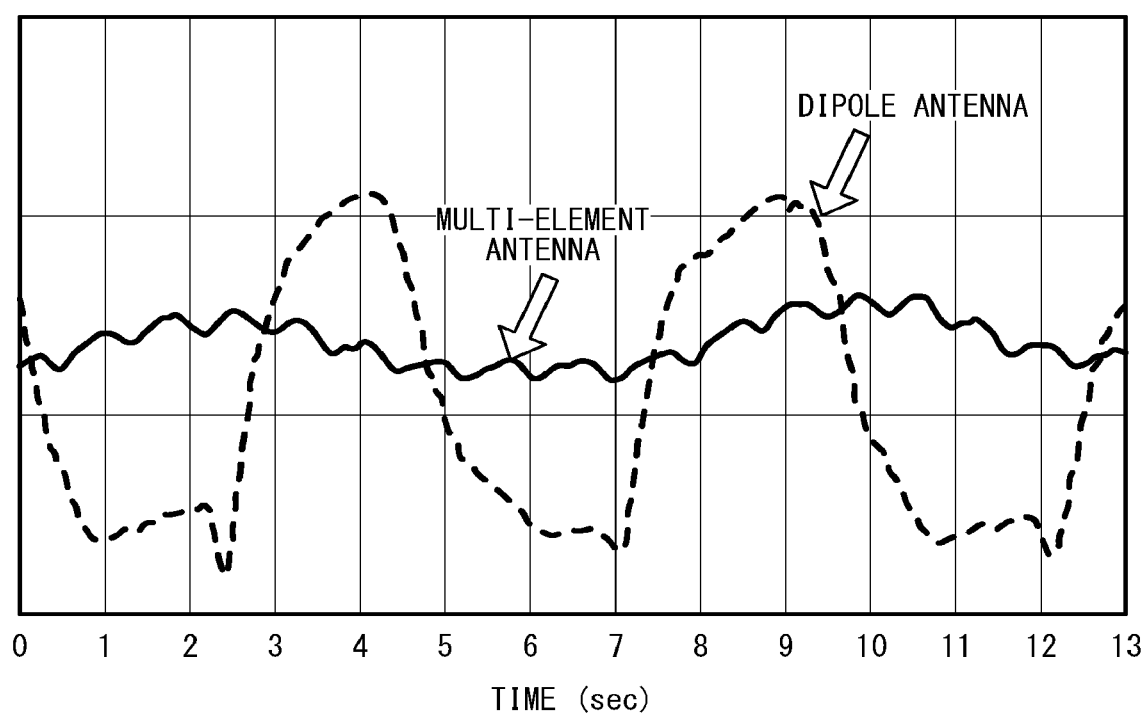
FIG. 21 is a graph of a measurement result that shows comparison of variation of the S11 parameter with respect to time between the multi-element antenna of the above-described embodiments and the conventional dipole antenna.

FIG. 21 is a graph of a measurement result that shows comparison of fluctuation of the S11 parameter with respect to time between the multi-element antenna of the present embodiment (indicated by the solid line) and the conventional dipole antenna (indicated by the broken line). In the conventional dipole antenna, fluctuation due to respiratory motions (i.e., fluctuations with a cycle of about 5 seconds) appears significantly and there may be a case where the fluctuation due to heartbeat is buried in the fluctuation due to the respiratory motions and cannot be detected.

Contrastively, in the multi-element antenna of the present embodiment, the fluctuation due to the respiratory motions is suppressed, and thus the fluctuation due to heartbeat (fluctuation with a cycle of less than 1 second), which is superimposed on the gradual and small fluctuation due to the respiratory motions, is clearly observed.

Thus, the biological information monitoring apparatus 1 using the multi-element antenna can detect the heartbeat while suppressing the influence of the respiratory motions, which may be a remarkable and beneficial effect of the present embodiments.

According to the biological information monitoring apparatus 1 of each embodiment described above, biological information such as heartbeat and respiration of the object can be stably detected with high reliability without imposing a burden on the object.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A biological information monitoring apparatus comprising:
    an antenna assembly including at least one antenna, the antenna assembly being configured to be disposed close to an object;
    a signal generator configured to generate a high-frequency signal;
    a coupling-amount detection circuit configured to detect a coupling amount of near-field coupling due to an electric field between the object and the at least one antenna by using the high-frequency signal; and
    a displacement detection circuit configured to detect a physical displacement of the object based on a change in the coupling amount of near-field coupling.

2. The biological information monitoring apparatus according to claim 1, wherein:
    the high-frequency signal generated by the signal generator is inputted to an input terminal of the at least one antenna; and
    the coupling-amount detection circuit is
        configured to detect the coupling amount of near-field coupling by measuring a reflected signal, the reflected signal being part of the high-frequency signal reflected at the input terminal of the at least one antenna, or
        configured to detect magnitude of a reflected signal from the input terminal of the at least one antenna as an S11 parameter indicating a reflection loss of the at least one antenna.

3. The biological information monitoring apparatus according to claim 1, wherein:
    the at least one antenna comprises a first antenna and a second antenna;
    the high-frequency signal generated by the signal generator is inputted to the first antenna; and
    the coupling-amount detection circuit is
        configured to measure a transmitted signal that is the high-frequency signal inputted to the first antenna and passes through to the second antenna and to detect the coupling amount of near-field coupling based on the transmitted signal, or
        configured to detect magnitude of a transmitted signal transmitted from the first antenna to the second antenna as an S21 parameter indicating an insertion loss from the first antenna to the second antenna.

4. The biological information monitoring apparatus according to claim 1, wherein the displacement detection circuit is configured to detect at least one of a heartbeat and a respiratory motion as the physical displacement of the object.

5. The biological information monitoring apparatus according to claim 1, wherein the at least one antenna is configured as a dipole antenna.

6. The biological information monitoring apparatus according to claim 2, wherein the at least one antenna is configured to have a voltage standing wave ratio (VSWR) in a range from 2.0 to 5.0.

7. The biological information monitoring apparatus according to claim 3, wherein:
    the first antenna is configured to have a voltage standing wave ratio (VSWR) in a range from 2.0 to 5.0; and
    the second antenna is configured to have the VSWR of 2.0 or less.

8. The biological information monitoring apparatus according to claim 2, wherein the at least one antenna is disposed close to a heart of the object when the at least one antenna consists of only one antenna.

9. The biological information monitoring apparatus according to claim 3, wherein:
    the at least one antenna comprises a plurality of antennas; and
    the plurality of antennas are disposed to sandwich a heart of the object in at least one of an anterior-posterior direction, a right-left direction, and a head-foot direction of the object.

10. The biological information monitoring apparatus according to claim 1, wherein the signal generator is configured to generate the high-frequency signal having a frequency corresponding to a resonance frequency related to a cardiac equivalent length inside the object.

11. The biological information monitoring apparatus according to claim 10, wherein:
    (A) the signal generator is configured to generate the high-frequency signal of a fundamental mode frequency, the fundamental mode frequency having a frequency that resonates in a fundamental mode with respect to the cardiac equivalent length, and the at least one antenna is configured to resonate at the fundamental mode frequency, or
    (B) the signal generator is configured to generate the high-frequency signal of a double mode frequency, the double mode frequency having a frequency that resonates in a double mode with respect to the cardiac equivalent length, and the at least one antenna is configured to resonate at the double mode frequency.

12. The biological information monitoring apparatus according to claim 10, wherein:
    the signal generator is configured to generate a first high-frequency signal of a fundamental mode frequency and a second high-frequency signal of a double mode frequency, the fundamental mode frequency having a frequency that resonates in a fundamental mode with respect to the cardiac equivalent length, and the double mode frequency having a frequency that resonates in a double mode with respect to the cardiac equivalent length;
    the at least one antenna comprises a first antenna configured to resonate at the fundamental mode frequency and a second antenna configured to resonate at the double mode frequency; and
    one of the first high-frequency signal and the second high-frequency signal is selected based on a result of a measurement performed beforehand.

13. The biological information monitoring apparatus according to claim 10, wherein:
    the antenna assembly is configured as a multi-resonant antenna having a plurality of resonance frequencies; and
    the signal generator is configured as a variable-frequency signal generator; and the signal generator is further configured to generate (i) the high-frequency signal of a frequency at which interference with a magnetic resonance signal is avoided, or (ii) the high-frequency signal having a frequency close to a resonance frequency based on a cardiac size of the object to be detected, among the plurality of resonance frequencies.

14. The biological information monitoring apparatus according to claim 10, wherein:
the at least one antenna is configured as a wideband antenna having a frequency bandwidth that covers a variation range of a resonance frequency based on variation in cardiac size between individuals; and
the signal generator is configured to be able to sweep a frequency of the high-frequency signal.

15. The biological information monitoring apparatus according to claim 1, wherein;
the signal generator is configured to generate the high-frequency signal having a resonance frequency that is determined by resonance length proportional to cardiac size of the object; and
the antenna assembly is configured as a multi-element antenna that includes a first element corresponding to the resonance frequency and at least one second element corresponding to a detuned frequency that is detuned by a predetermined frequency from the resonance frequency.

16. An MRI apparatus comprising the biological information monitoring apparatus according to claim 1.

17. The MRI apparatus according to claim 16, wherein the displacement detection circuit is configured to detect the physical displacement of the object at a timing that overlaps with neither an RF transmission period nor an MR reception period, the RF transmission period being a period during which the MRI apparatus applies an RF pulse to the object, and the MR reception period being a period during which the MRI apparatus receives a magnetic resonance signal from the object.

18. The MRI apparatus according to claim 16, wherein the displacement detection circuit is configured to detect the physical displacement of the object at intervals of 250 milliseconds or less.

19. The MRI apparatus according to claim 16, wherein a frequency of the high-frequency signal generated by the signal generator is set higher than a Larmor frequency used by the MRI apparatus.

20. The MRI apparatus according to claim 16, wherein:
the at least one antenna is embedded in at least one of a table and an RF coil of the MRI apparatus; and
the at least one of a table and an RF coil is provided with marking in such a manner that a position of the at least one antenna embedded therein is visible.

* * * * *